US012773251B2

(12) United States Patent
Pang et al.

(10) Patent No.: US 12,773,251 B2
(45) Date of Patent: Oct. 27, 2026

(54) CRYOABLATION TEMPERATURE CONTROL METHOD, SYSTEM AND COMPUTER-READABLE STORAGE MEDIUM

(71) Applicant: SHANGHAI MICROPORT EP MEDTECH CO., LTD., Shanghai (CN)

(72) Inventors: Degui Pang, Shanghai (CN); Liuping Shen, Shanghai (CN); Jinfeng Liu, Shanghai (CN); Chen Cheng, Shanghai (CN); Chuang Zhao, Shanghai (CN); Yuanxing Xu, Shanghai (CN)

(73) Assignee: SHANGHAI MICROPORT EP MEDTECH CO., LTD., Shanghai (CN)

( * ) Notice: Subject to any disclaimer, the term of this patent is extended or adjusted under 35 U.S.C. 154(b) by 1381 days.

(21) Appl. No.: 17/611,840

(22) PCT Filed: Apr. 23, 2021

(86) PCT No.: PCT/CN2021/089198
§ 371 (c)(1),
(2) Date: Nov. 16, 2021

(87) PCT Pub. No.: WO2021/258840
PCT Pub. Date: Dec. 30, 2021

(65) Prior Publication Data
US 2022/0304737 A1 Sep. 29, 2022

(30) Foreign Application Priority Data
Jun. 23, 2020 (CN) ........................ 202010576984.3

(51) Int. Cl.
*A61B 18/02* (2006.01)
*A61B 18/00* (2006.01)

(52) U.S. Cl.
CPC ...... *A61B 18/02* (2013.01); *A61B 2018/0022* (2013.01); *A61B 2018/00351* (2013.01);
(Continued)

(58) Field of Classification Search
CPC ........... A61B 2018/00648; A61B 2018/00666; A61B 2018/00714; A61B 2018/00744;
(Continued)

(56) References Cited

U.S. PATENT DOCUMENTS

2009/0088735 A1 4/2009 Abboud
2010/0042086 A1 2/2010 Reynolds
(Continued)

FOREIGN PATENT DOCUMENTS

CN 103025377 A 4/2013
CN 103547229 A 1/2014
(Continued)

OTHER PUBLICATIONS

Song, Mingyang, "The Control Methor Study and Software Design of Alternated Cooling and heating Treatment Publication Name: China Master's Theses Full-text Database" Publication Date: Jul. 15, 2012 , 60 pages.

*Primary Examiner* — Jaymi E Della
(74) *Attorney, Agent, or Firm* — Muncy, Geissler, Olds & Lowe, P.C.

(57) ABSTRACT

A cryoablation temperature control method, system and computer-readable storage medium. The method is used to control a temperature of the interior of a cryoablation balloon and includes: generating a first target liquid inlet pressure control signal for controlling a liquid supply flow rate of a high-pressure proportional valve in a liquid supply channel for the balloon; generating a first target gas outlet pressure control signal for controlling a gas outlet flow rate of a low-pressure proportional valve in the gas outlet chan-
(Continued)

nel for the balloon and for coordinating with the first target liquid inlet pressure control signal to perform control so that a pressure in the interior of the balloon is within a predefined safe pressure threshold value range and the temperature of the interior of the balloon is brought to and/or maintained at the target temperature value.

14 Claims, 8 Drawing Sheets

(52) U.S. Cl.
CPC ............... *A61B 2018/00577* (2013.01); *A61B 2018/00648* (2013.01); *A61B 2018/00666* (2013.01); *A61B 2018/00714* (2013.01); *A61B 2018/00744* (2013.01); *A61B 2018/00791* (2013.01); *A61B 2018/00863* (2013.01); *A61B 2018/0212* (2013.01); *A61B 2018/0262* (2013.01)

(58) Field of Classification Search
CPC ........... A61B 2018/00791; A61B 2018/00863; A61B 18/02; A61B 2018/0022; A61B 2018/0212; A61B 2018/0231–2018/0293
See application file for complete search history.

(56) References Cited

U.S. PATENT DOCUMENTS

| | | | | |
|---|---|---|---|---|
| 2012/0029495 | A1 | 2/2012 | Wittenberger | |
| 2013/0231650 | A1 | 9/2013 | Watson | |
| 2021/0177484 | A1 * | 6/2021 | Tegg | A61B 18/02 |
| 2021/0307804 | A1 * | 10/2021 | Lalonde | A61B 18/02 |
| 2022/0287757 | A1 * | 9/2022 | Gong | A61B 18/02 |

FOREIGN PATENT DOCUMENTS

| | | | | |
|---|---|---|---|---|
| CN | 107307901 A | | 11/2017 | |
| CN | 107951559 A | | 4/2018 | |
| CN | 109674525 A | | 4/2019 | |
| CN | 110464444 A | | 11/2019 | |
| CN | 111529047 A | | 8/2020 | |
| CN | 112263321 A | | 1/2021 | |
| WO | WO-2019083764 A1 | * | 5/2019 | A61B 18/02 |

* cited by examiner

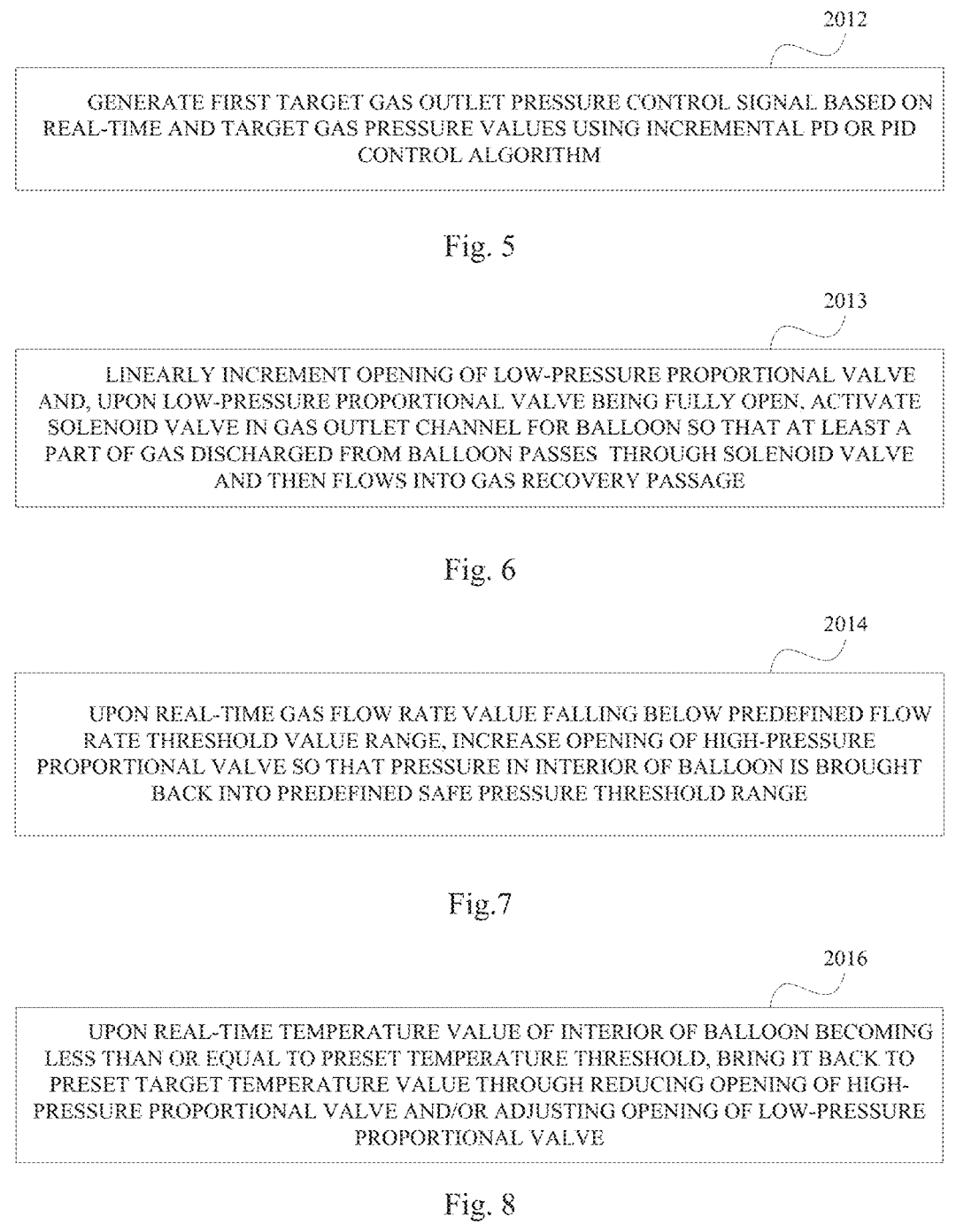

2012

GENERATE FIRST TARGET GAS OUTLET PRESSURE CONTROL SIGNAL BASED ON REAL-TIME AND TARGET GAS PRESSURE VALUES USING INCREMENTAL PD OR PID CONTROL ALGORITHM

Fig. 5

2013

LINEARLY INCREMENT OPENING OF LOW-PRESSURE PROPORTIONAL VALVE AND, UPON LOW-PRESSURE PROPORTIONAL VALVE BEING FULLY OPEN, ACTIVATE SOLENOID VALVE IN GAS OUTLET CHANNEL FOR BALLOON SO THAT AT LEAST A PART OF GAS DISCHARGED FROM BALLOON PASSES THROUGH SOLENOID VALVE AND THEN FLOWS INTO GAS RECOVERY PASSAGE

Fig. 6

2014

UPON REAL-TIME GAS FLOW RATE VALUE FALLING BELOW PREDEFINED FLOW RATE THRESHOLD VALUE RANGE, INCREASE OPENING OF HIGH-PRESSURE PROPORTIONAL VALVE SO THAT PRESSURE IN INTERIOR OF BALLOON IS BROUGHT BACK INTO PREDEFINED SAFE PRESSURE THRESHOLD RANGE

Fig.7

2016

UPON REAL-TIME TEMPERATURE VALUE OF INTERIOR OF BALLOON BECOMING LESS THAN OR EQUAL TO PRESET TEMPERATURE THRESHOLD, BRING IT BACK TO PRESET TARGET TEMPERATURE VALUE THROUGH REDUCING OPENING OF HIGH-PRESSURE PROPORTIONAL VALVE AND/OR ADJUSTING OPENING OF LOW-PRESSURE PROPORTIONAL VALVE

Fig. 8

CRYOABLATION TEMPERATURE CONTROL METHOD, SYSTEM AND COMPUTER-READABLE STORAGE MEDIUM

CROSS-REFERENCE TO RELATED APPLICATION

This application claims priority to Chinese Patent Application No. 2020105769843, filed with the China National Intellectual Property Administration (CNIPA) on Jun. 23, 2020, entitled "CRYOABLATION TEMPERATURE CONTROL METHOD, SYSTEM AND MEDIUM", which is incorporated herein by reference in its entirety.

TECHNICAL FIELD

This application pertains to the field of medical instruments technology, and relates in particular to a cryoablation temperature control method, system and computer-readable storage medium.

BACKGROUND

Cryoablation, as a new therapeutic technique for the treatment of atrial fibrillation, has received widespread attention in recent years. Arrhythmia treatment by cryoablation is achieved by destroying a target site identified as a source of aberrant electrophysiological activity associated with arrhythmia by applying to the site a cryogenic liquid, which absorbs by evaporation and takes away heat from tissue at the site and thereby lowers its temperature and "freezes and kills" cells there. A lot of clinical data has shown that, compared to other ablation techniques, cryoablation allows easier physician learning and operation, a shorter procedure time, improved treatment effectiveness, reduced risk of the occurrence of thrombosis and other serious complications, and less patient pain.

However, traditional cryoablation systems tend to employ a constant flow rate control scheme during a settlement phase of an ablation process, leading to a proportionally lower temperature resulting from a longer ablation time and making it impossible to maintain a desired low temperature for a desirable length of time. In order to avoid any risk, the ablation process has to be interrupted to wait for recovery of the temperature to the target value and may require several such cycles. This leads not only to increased operational complexity and a prolonged procedure time but increased surgical risk, unsatisfactory pulmonary vein isolation (PVI) effects and significant side effects to the affected tissue. The increasing demand for cryoablation procedures calls for substantial enhancement of low temperature control as required by these procedures. Therefore, there is an urgent need for a technique capable of maintaining a desired temperature and volume ablation rate of a balloon used in a cryoablation procedure and resulting in good PVI effects while avoiding tissue damage caused by deformation of the balloon.

SUMMARY OF THE INVENTION

In view of the above-discussed problems with the prior art, it is desirable to provide a cryoablation temperature control method, system and computer-readable storage medium capable of bringing a temperature of the interior of a balloon to, and maintaining it at, a preset temperature value and allowing a short procedure time, easy operation, improved pulmonary vein isolation (PVI) effects and avoided damage to tissue arising from deformation of the balloon.

In a first aspect of this application, there is provided a cryoablation temperature control method for controlling a temperature of the interior of a cryoablation balloon. The method comprises: acquiring a real-time temperature value and a preset target temperature value of the interior of the balloon, and generating a first temperature control signal based on the real-time and target temperature values;

acquiring a real-time gas flow rate value and a target gas flow rate value of a gas recovery passage in a gas outlet channel for the balloon, and generating a first gas flow rate control signal based on the real-time and target gas flow rate values;

generating, based on the first temperature control signal and/or the first gas flow rate control signal, a first target liquid inlet pressure control signal for controlling a liquid supply flow rate of a high-pressure proportional valve in a liquid supply channel for the balloon through collaboration of temperature control and flow rate control;

acquiring a real-time gas pressure value on, and a preset target gas pressure value for, a gas outlet side of the balloon; and generating, based on the real-time and target gas pressure values, a first target gas outlet pressure control signal for controlling a gas outlet flow rate of a low-pressure proportional valve in the gas outlet channel for the balloon and for controlling, together with the first target liquid inlet pressure control signal, the liquid supply flow rate of the high-pressure proportional valve, so that a pressure in the interior of the balloon is within a predefined safe pressure threshold value range and the temperature of the interior of the balloon is brought to and/or maintained at the target temperature value.

According to this embodiment, seamless switching between flow rate control and temperature control is achieved by the first target liquid inlet pressure control signal generated based on: the first temperature control signal generated based on the acquired real-time temperature value and target temperature value of the interior of the cryoablation balloon; and/or the first gas flow rate control signal generated based on the acquired real-time gas flow rate value and target gas flow rate value of the gas recovery passage in the gas outlet channel for the balloon. Controlling the liquid supply flow rate of the high-pressure proportional valve in the liquid supply channel for the balloon through collaboration of temperature control and flow rate control and controlling the gas outlet flow rate of the low-pressure proportional valve in the gas outlet channel for the balloon based on the acquired real-time gas pressure value on, and preset target gas pressure value for, the gas outlet side of the balloon in a dynamically collaborative way can bring the temperature of the interior of the balloon to, and maintain it at, the preset target temperature value, thus resulting in improved PVI effects. The collaboration of temperature control and flow rate control reduces operational complexity, required procedure time and surgical risk. The preset target gas pressure value, to which the gas pressure value on the gas outlet side of the balloon is brought, and at which this value is maintained, by dynamically controlling the gas outlet flow rate of the low-pressure proportional valve, keeps the pressure in the interior of the balloon above the ambient atmospheric pressure and below a relief pressure for the balloon, avoiding the risk of tearing of the tissue against which the balloon is pressed due to a too low pressure in the interior of the balloon and the risk of bursting of the balloon due to a too high pressure in the interior of the balloon. Compared with traditional systems or apparatuses that simply rely on temperature control, this application provides a user with options with collaboration of and seamless switching between temperature control and flow rate control (i.e., options for flow rate control, temperature control and combined temperature and flow rate control). Thus, the inventive product has improved utility and increased convenience of use by allowing the user to choose a suitable control method for a particular surgical procedure. With this application, flow rate control and temperature control can be conducted in a dynamically collaborative manner, which can reduce the required procedure time and operational complexity, keep the pressure in the interior of the balloon within the predefined safe pressure threshold value range, and bring the temperature of the interior of the balloon to, and/or maintain it, at the target temperature value. Apart from this, in addition to faster and more accurate temperature control within a wider range, the balloon's interior pressure can be maintained at a proper value that avoids the risk of tearing of the tissue against which the balloon is pressed due to a too low pressure and the risk of bursting of the balloon due to a too high pressure. Thus, the balloon can operate more stably to result in improved PVI effects and reduced risk and side effects associated with the cryoablation procedure.

In one embodiment, the cryoablation temperature control method may further comprise:

- generating the first temperature control signal based on the real-time and target temperature values using an incremental proportional-derivative (PD) or proportional-integral-derivative (PID) control algorithm;
- generating the first gas flow rate control signal based on the real-time and target gas flow rate values using an incremental PD or PID control algorithm; and
- generating, based on the first temperature control signal and/or the first gas flow rate control signal, the first target liquid inlet pressure control signal for controlling the liquid supply flow rate of the high-pressure proportional valve.

In one embodiment, controlling the liquid supply flow rate of the high-pressure proportional valve may comprise:

- acquiring a real-time liquid pressure value on a liquid outlet side of the high-pressure proportional valve; and
- generating a second target liquid inlet pressure control signal for controlling the liquid supply flow rate of the high-pressure proportional valve based on the first target liquid inlet pressure control signal and the real-time liquid pressure value.

According to this embodiment, the temperature of the interior of the balloon can be brought to and/or maintained at the target temperature value by dynamically controlling the liquid supply flow rate of the high-pressure proportional valve based on the second target liquid inlet pressure control signal generated based on the real-time liquid pressure value acquired on the liquid outlet side of the high-pressure proportional valve arranged on a liquid supply side of the balloon and based on a target value indicated in the first target liquid inlet pressure control signal. The cryoablation temperature control based on the dynamical control of the liquid supply flow rate of the high-pressure proportional valve based on the second target liquid inlet pressure control signal generated based on the real-time liquid pressure value on the liquid outlet side of the high-pressure proportional valve and based on the first target liquid inlet pressure control signal is accomplished by either or both of flow rate control and temperature control. In this way, seamless switching between flow rate control and temperature control is achievable. In the current practice, physicians are used to flow rate control, which, however, leads to continual decreasing of temperature. In the absence of temperature control that allows the temperature to be maintained at a desired value, the ablation process has to be interrupted possibly for several times, leading to a prolonged time of the balloon staying within the patient's body. Therefore, the coordinated use of, and thus seamless switching between, flow rate control and temperature control according to this embodiment can result in a significant reduction in the required procedure time.

In one embodiment, controlling the liquid supply flow rate of the high-pressure proportional valve may comprise:

- acquiring a real-time liquid pressure value on a liquid outlet side of the high-pressure proportional valve;
- calculating a target liquid pressure value for the liquid outlet side of the high-pressure proportional valve based on the first target liquid inlet pressure control signal; and
- generating a second target liquid inlet pressure control signal for controlling the liquid supply flow rate of the high-pressure proportional valve based on the real-time liquid pressure value and the target liquid pressure value using an incremental PD or PID control algorithm.

According to this embodiment, calculating the target liquid pressure value for the liquid outlet side of the high-pressure proportional valve based on the first target liquid inlet pressure control signal and generating the second target liquid inlet pressure control signal using an incremental PD or PID control algorithm enables seamless switching between flow rate control and temperature control and hence dynamical control of the liquid supply flow rate of the high-pressure proportional valve, which addresses both temperature control and flow rate control needs and allows the temperature of the interior of the balloon to be brought to and/or maintained at the target temperature value, with increased coordination between the multiple control parameters, reduced operational complexity and a shortened time required for the procedure.

In one embodiment, generating the first target gas outlet pressure control signal for controlling the gas outlet flow rate of the low-pressure proportional valve in the gas outlet channel for the balloon based on the real-time and target gas pressure values may comprise:

- generating the first target gas outlet pressure control signal based on the real-time and target gas pressure values using an incremental PD or PID control algorithm.

According to this embodiment, dynamically controlling the gas outlet flow rate of the low-pressure proportional valve using an incremental PD or PID control algorithm keeps the pressure in the interior of the balloon within the predefined safe pressure threshold value range, e.g., at a value above the ambient atmospheric pressure and below the relief pressure of the balloon, which avoids the risk of tearing of the tissue against which the balloon is pressed due to a too low pressure and the risk of bursting of the balloon due to a too high pressure.

In one embodiment, the cryoablation temperature control method may further comprise predicting a slope of a profile of the real-time gas flow rate value to control the target gas low rate value and dividing a temperature control process into at least two phases including a rapid temperature drop phase and a slow temperature drop phase based on the real-time temperature value, wherein in the slow temperature drop phase, the real-time gas flow rate value is maintained in to a predefined stable flow rate threshold value range for the real-time gas flow rate value.

In one embodiment, controlling the gas outlet flow rate of the low-pressure proportional valve in the gas outlet channel for the balloon may comprise:

in the event of the real-time gas flow rate value falling below a predefined flow rate threshold value range, increasing an opening of the high-pressure proportional valve so that the pressure in the interior of the balloon is brought back into the predefined safe pressure threshold range.

According to this embodiment, whenever the real-time gas flow rate value drops below the predefined flow rate threshold value range, the pressure in the interior of the balloon is increased and brought back into the safe pressure threshold value range to avoid tearing of the tissue against which the balloon is pressed due to excessive shrinkage of the balloon in the course of cryoablation. In this way, both stable supply and discharge flow rates can be ensured for the balloon while keeping the pressure in the interior of the balloon within the safe pressure threshold value range.

In one embodiment, the cryoablation temperature control method may further comprise:

- in the event of the real-time temperature value of the interior of the balloon becoming less than or equal to a preset temperature threshold, thereby bringing it back to the preset target temperature value through reducing an opening of the high-pressure proportional valve and/or adjusting an opening of the low-pressure proportional valve.

According to this embodiment, when the real-time temperature value of the interior of the balloon becomes less than or equal to the preset temperature threshold value, the high-pressure proportional valve and/or low-pressure proportional valve can be switched to a rewarming/protection mode to avoid causing damage to the tissue due to a too low temperature.

In a second aspect of this application, there is provided a cryoablation temperature control method for controlling a pressure in the interior of a cryoablation balloon. The method comprises:

- acquiring a real-time gas flow rate value of a gas recovery passage in a gas outlet channel for the balloon;
- if the real-time gas flow rate value is within a predefined stable flow rate threshold value range, linearly incrementing an opening of a low-pressure proportional valve in the gas outlet channel for the balloon; and
- upon the low-pressure proportional valve being fully open, activating a solenoid valve in the gas outlet channel for the balloon so that at least a part of a gas discharged from the balloon passes through the solenoid valve and then flows into the gas recovery passage, thereby bringing the pressure in the interior of the balloon into a predefined safe pressure threshold value range.

According to this embodiment, flow rate control of the balloon may begin with rapidly decreasing the temperature of the interior of the balloon, and when the real-time gas flow rate value drops below the predefined flow rate threshold value range, the opening of the high-pressure proportional valve may be increased to raise the liquid supply flow rate and thereby bring the pressure in the interior of the balloon back into the predefined safe pressure threshold value range. During the rapid decrease of the temperature of the interior of the balloon, when the detected real-time gas flow rate value drops into the predefined stable flow rate threshold value range, the slow temperature drop phase may be initiated. In this phase, the real-time gas flow rate value can be kept within the stable flow rate threshold value range, and the opening of the low-pressure proportional valve may be linearly incremented. When the low-pressure proportional valve is fully open, the solenoid valve in the gas outlet channel for the balloon may be activated to switch to a mode in which the solenoid valve is controlled to allow the temperature of the interior of the balloon to slowly drop to the preset target temperature value and the pressure in the interior of the balloon is maintained. This allows more stable flow rate transitioning without abrupt fluctuations.

In one embodiment, upon the low-pressure proportional valve being fully open, the low-pressure proportional valve may be deactivated at the same time as the activation of the solenoid valve in the gas outlet channel for the balloon so that the gas discharged from the balloon entirely passes through the solenoid valve and then flows into the gas recovery passage, thereby bringing the pressure in the interior of the balloon into the predefined safe pressure threshold value range. This can avoid the problem of significant flow rate fluctuations.

In a third aspect of this application, there is provided a cryoablation temperature control system for controlling a temperature of the interior of a cryoablation balloon. The system comprises:

- a temperature sensor for capturing a real-time temperature value of the interior of the balloon;
- a high-pressure proportional valve disposed in a liquid supply channel for the balloon;
- a first pressure sensor disposed in a gas outlet channel for the balloon, wherein the first pressure sensor is configured to capture a real-time gas pressure value on a gas outlet side of the balloon;
- a low-pressure proportional valve disposed in the gas outlet channel for the balloon, wherein the low-pressure proportional valve is configured to adjust the pressure of a gas in the interior of the balloon;
- a flow rate sensor disposed in the gas outlet channel for the balloon, the flow rate sensor configured to capture a real-time gas flow rate value of a gas recovery passage in the gas outlet channel for the balloon; and
- a controller coupled to each of the temperature sensor, the high-pressure proportional valve, the first pressure sensor, the low-pressure proportional valve and the flow rate sensor,
- wherein the controller is configured to:
- acquire the real-time temperature value and a preset target temperature value of the interior of the balloon, and generate a first temperature control signal from the real-time and target temperature values; acquire the real-time gas flow rate value and a target gas flow rate value of the gas recovery passage in the gas outlet channel for the balloon, and generate a first gas flow rate control signal from the real-time and target gas flow rate values; and generate, based on the first temperature control signal and/or the first gas flow rate control signal, a first target liquid inlet pressure control signal for controlling a liquid supply flow rate of the high-pressure proportional valve in the liquid supply channel for the balloon through collaboration of temperature control and flow rate control; and
- acquire a real-time gas pressure value on, and a preset target gas pressure value for, the gas outlet side of the balloon and generate, based on the real-time and target gas pressure values, a first target gas outlet pressure control signal for controlling a gas outlet flow rate of the low-pressure proportional valve and for controlling, together with the first target liquid inlet pressure control signal, the liquid supply flow rate of the high-pressure proportional valve, so that a pressure in the interior of the balloon is within a predefined safe pressure threshold value range and the temperature of the interior of the balloon is brought to and/or maintained at the target temperature value.

According to this embodiment, the controller may control the liquid supply flow rate of the high-pressure proportional valve in the liquid supply channel for the balloon based on the acquired real-time temperature value and target temperature value of the interior of the cryoablation balloon and, as well as on the acquired real-time gas flow rate value and target gas flow rate value of the gas recovery passage in the gas outlet channel for the balloon in a dynamically collaborative way, and may further control the gas outlet flow rate of the low-pressure proportional valve in the gas outlet channel for the balloon based on the acquired real-time gas pressure value on, and the preset target gas pressure value for, the gas outlet side of the balloon in a dynamically collaborative way control. As a result, the temperature of the interior of the balloon can be brought to and maintained at the preset target temperature value, resulting in improved PVI effects and reduced operational complexity, procedure time and surgical risk. The preset target gas pressure value, to which the gas pressure value on the gas outlet side of the balloon is brought, and at which this value is maintained, by dynamically controlling the gas outlet flow rate of the low-pressure proportional valve, keeps the pressure in the interior of the balloon above the ambient atmospheric pressure and below a relief pressure for the balloon, avoiding the risk of tearing of the tissue against which the balloon is pressed due to a too low pressure in the interior of the balloon and the risk of bursting of the balloon due to a too high pressure in the interior of the balloon.

In one embodiment, the controller may be further configured to:

generate the first temperature control signal based on the real-time and target temperature values using an incremental PD or PID control algorithm;

generate the first gas flow rate control signal based on the real-time and target gas flow rate values using the incremental PD or PID control algorithm;

generate, based on the first temperature control signal and/or the first gas flow rate control signal, the first target liquid inlet pressure control signal for controlling the liquid supply flow rate of the high-pressure proportional valve; and acquire the real-time gas pressure value on, and the preset target gas pressure value for, the gas outlet side of the balloon and generate, based on the real-time and target gas pressure values, the first target gas outlet pressure control signal for controlling the gas outlet flow rate of the low-pressure proportional valve using the incremental PD or PID control algorithm.

According to this embodiment, dynamically controlling the temperature of the interior of the balloon value to the preset temperature value by the controller using an incremental PD or PID control algorithm allows a rapid decrease in temperature and differential prediction of how the liquid supply flow rate rises, avoiding overshoot of liquid supply flow rate. Dynamically controlling the gas flow rate on the gas outlet side of the balloon by the controller using an incremental PD or PID control algorithm allows dividing the gas flow rate profile into a number of segments, for each of which, a slope of the gas flow rate may be predicted to serve as a basis for controlling the flow rate to rise. This results in more accurate gas flow rate control and more stable maintenance of the flow rate on the gas outlet side of the balloon. By bringing the gas pressure on the gas outlet side of the balloon to, and maintaining it at, the preset target gas pressure value through dynamically controlling the gas outlet flow rate of the low-pressure proportional valve using an incremental PD or PID control algorithm, the pressure in the interior of the balloon can be maintained at a value above the ambient atmospheric pressure and below a relief pressure of the balloon, which avoids the risk of tearing of the tissue against which the balloon is pressed due to a too low pressure and the risk of bursting of the balloon due to a too high pressure.

In one embodiment, the cryoablation temperature control system may further comprise a second pressure sensor disposed in a liquid inlet channel for the balloon, wherein the second pressure sensor is coupled to the controller and the second pressure sensor is configured to capture a real-time liquid pressure value on a liquid outlet side of the high-pressure proportional valve, wherein the controller is further configured to:

acquire the real-time liquid pressure value and generate, based on the first target liquid inlet pressure control signal and the real-time liquid pressure value, a second target liquid inlet pressure control signal for controlling the liquid supply flow rate of the high-pressure proportional valve.

According to this embodiment, the controller can bring the temperature of the interior of the balloon to and/or maintain it at the target temperature value by dynamically controlling the liquid supply flow rate of the high-pressure proportional valve based on the real-time liquid pressure value acquired on the liquid outlet side of the high-pressure proportional valve arranged on a liquid supply side of the balloon and a target value indicated in the first target liquid inlet pressure control signal.

In one embodiment, the controller may comprise a parameter acquisition module, a liquid supply flow rate control module and a gas outlet pressure control module. The parameter acquisition module may be configured to acquire the real-time temperature value and the preset target temperature value of the interior of the balloon, the real-time gas flow rate value and the target gas flow rate value of the gas recovery passage in the gas outlet channel for the balloon, and the real-time gas pressure value on, and the preset target gas pressure value for, the gas outlet side of the balloon. The liquid supply flow rate control module may be configured to: generate the first temperature control signal based on the real-time and target temperature values; generate the first gas flow rate control signal based on the real-time and target gas flow rate values; and generate, based on the first temperature control signal and/or the first gas flow rate control signal, the first target liquid inlet pressure control signal for controlling the liquid supply flow rate of the high-pressure proportional valve in the liquid supply channel for the balloon through collaboration of temperature control and flow rate control. The gas outlet pressure control module may be configured to generate, based on the real-time and target gas pressure values, the first target gas outlet pressure control signal for controlling the gas outlet flow rate of the low-pressure proportional valve in the gas outlet channel for the balloon. The liquid supply flow rate control module and the gas outlet pressure control module may coordinate with each other to perform control so that the pressure in the interior of the balloon is within the predefined safe pressure threshold value range and the temperature of the interior of the balloon is brought to and/or maintained at the target temperature value.

In one embodiment, the parameter acquisition module may be further configured to acquire a real-time liquid pressure value on a liquid outlet side of the high-pressure proportional valve.

The liquid supply flow rate control module may comprise:

a temperature PD/PID control module configured to generate the first temperature control signal based on the real-time and target temperature values using an incremental PD or PID control algorithm;

a gas flow rate PD/PID control module configured to generate the first gas flow rate control signal based on the real-time and target gas flow rate values using an incremental PD or PID control algorithm; and a high-pressure proportional valve PD/PID control module configured to: generate the first target liquid inlet pressure control signal based on the first temperature control signal and/or the first gas flow rate control signal; calculate a target liquid pressure value for the liquid outlet side of the high-pressure proportional valve based on the first target liquid inlet pressure control signal; and generate, based on the real-time and target liquid pressure values using an incremental PD or PID control algorithm, a second target liquid inlet pressure control signal for controlling the liquid supply flow rate of the high-pressure proportional valve.

The gas outlet pressure control module may comprise a low-pressure proportional valve PD/PID control module configured to generate, based on the real-time and target gas pressure values using an incremental PD or PID control algorithm, the first target gas outlet pressure control signal for controlling the gas outlet flow rate of the low-pressure proportional valve.

The temperature PD/PID control module, the gas flow rate PD/PID control module, the high-pressure proportional valve PD/PID control module and the low-pressure proportional valve PD/PID control module may coordinate with one another to perform control so that the pressure in the interior of the balloon is within the predefined safe pressure threshold value range and the temperature of the interior of the balloon is brought to and/or maintained at the target temperature value.

According to this embodiment, the coordinated control of the temperature PD/PID control module, the gas flow rate PD/PID control module, the high-pressure proportional valve PD/PID control module and the low-pressure proportional valve PD/PID control module enables seamless switching between flow rate control and temperature control, resulting in a significant reduction in the required procedure time.

In one embodiment, the controller may be further configured to:

in the event of the real-time temperature value of the interior of the balloon becoming less than or equal to a preset temperature threshold value, bringing it back to the preset target temperature value through reducing an opening of the high-pressure proportional valve and/or adjusting an opening of the low-pressure proportional valve.

According to this embodiment, when the real-time temperature value of the interior of the balloon becomes less than or equal to a preset temperature threshold value, the controller is configured to activate a rewarming/protection mode of the high-pressure proportional valve and/or the low-pressure proportional valve, which avoids causing unnecessary damage to the tissue due to an excessively low temperature.

In a fourth aspect of this application, there is provided a cryoablation temperature control system for controlling a pressure in the interior of a cryoablation balloon. The system comprises:

a low-pressure proportional valve disposed in a gas outlet channel for the balloon, wherein the low-pressure proportional valve is configured to adjust a gas pressure value in the interior of the balloon;

a solenoid valve disposed in the gas outlet channel for the balloon, wherein the solenoid valve is in parallel with the low-pressure proportional valve;

a flow rate sensor disposed in the gas outlet channel for the balloon, wherein the flow rate sensor is configured to capture a real-time gas flow rate value of a gas recovery passage in the gas outlet channel for the balloon; and a controller coupled to each of the low-pressure proportional valve, the solenoid valve and the flow rate sensor, the controller configured to:

acquire the real-time gas flow rate value of the gas recovery passage in the gas outlet channel for the balloon;

linearly increment an opening of the low-pressure proportional valve in the gas outlet channel for the balloon if the real-time gas flow rate value is within a predefined stable flow rate threshold range; and upon the low-pressure proportional valve being fully open, activate the solenoid valve in the gas outlet channel for the balloon so that at least a part of a gas discharged from the balloon passes through the solenoid valve and then flows into the gas recovery passage.

In one embodiment, the controller may be further configured to deactivate the low-pressure proportional valve at the same time as the activation of the solenoid valve in the gas outlet channel for the balloon upon the low-pressure proportional valve being fully open so that the gas discharged from the balloon entirely passes through the solenoid valve and then flows into the gas recovery passage, thereby bringing the pressure in the interior of the balloon into a predefined safe pressure threshold value range.

According to this embodiment, the controller may instruct to linearly increment the opening of the low-pressure proportional valve upon the real-time gas flow rate value shifting into the predefined stable flow rate threshold value range and to activate the solenoid valve in the gas outlet channel for the balloon upon the low-pressure proportional valve becoming fully open so that at least a part of the gas discharged from the balloon passes through the solenoid valve into the gas recovery passage. Alternatively, upon the low-pressure proportional valve being fully open, the controller may instruct to activate the solenoid valve in the gas outlet channel for the balloon and simultaneously deactivate the low-pressure proportional valve so as to be able to determine proportional coefficients for linearly incrementing the opening of the low-pressure proportional valve based on slopes of change in flow rate. This can avoid flow rate overshoot of the low-pressure proportional valve due to an excessively rapid rising rate of the flow rate, and avoid too much time taken by the flow rate of the low-pressure proportional valve to reach a target value due to an excessively slow rising rate of the flow rate. Further, it allows the flow rate of the low-pressure proportional valve to increase more steadily without significant fluctuations.

In one embodiment, the cryoablation temperature control system may further comprise a high-pressure proportional valve disposed in a liquid supply channel for the balloon and coupled to the controller, and the controller may be further configured to increase an opening of the high-pressure proportional valve in the event of the real-time gas flow rate value falling below a predefined flow rate threshold value range so that the pressure in the interior of the balloon is brought back into the predefined safe pressure threshold range.

In a fifth aspect of this application, there is provided a computer-readable storage medium having a computer program stored thereon, wherein upon execution of the computer program by a processor, the steps in the method according to any of the above embodiment are implemented.

BRIEF DESCRIPTION OF THE DRAWINGS

In order to more clearly explain embodiments of the present application, the accompanying drawings, to which reference is to be made in connection with the following description of embodiments, will be briefed below. Apparently, these drawings show only some embodiments of the present application, and those of ordinary skill in the art can obtain other drawings in light of those contained herein, without paying any creative effort.

FIG. 5 shows a flowchart of a cryoablation temperature control method according to a fifth embodiment of the present application.

FIG. 6 shows a flowchart of a cryoablation temperature control method according to a sixth embodiment of the present application.

FIG. 7 shows a flowchart of a cryoablation temperature control method according to a seventh embodiment of the present application.

FIG. 8 shows a flowchart of a cryoablation temperature control method according to an eighth embodiment of the present application.

DETAILED DESCRIPTION

This application will be described more fully hereinafter with reference to the accompanying drawings in order to facilitate understanding thereof, in which preferred embodiments of the application are shown. This application may, however, be embodied in many different forms and should not be construed as limited to the embodiments set forth herein. Rather, these embodiments are provided so that the disclosure will be thorough and complete.

Unless otherwise defined, all technical and scientific terms used herein have the same meaning as commonly understood by one having ordinary skill in the art to which this application belongs. The terminology used in the specification of the present application is for the purpose of describing particular embodiments only and is not intended to be limiting of the present application. As used herein, the term "and/or" includes any and all combinations of one or more of the associated listed items.

The terms "comprising", "having" and "including", when used in this specification, do not preclude the addition of one or more other components, unless further defined with the term "only", "consisting of" or the like. As used herein, the singular forms "a", "an" and "the" are intended to include the plural forms as well, unless the context clearly indicates otherwise.

Figure 1:
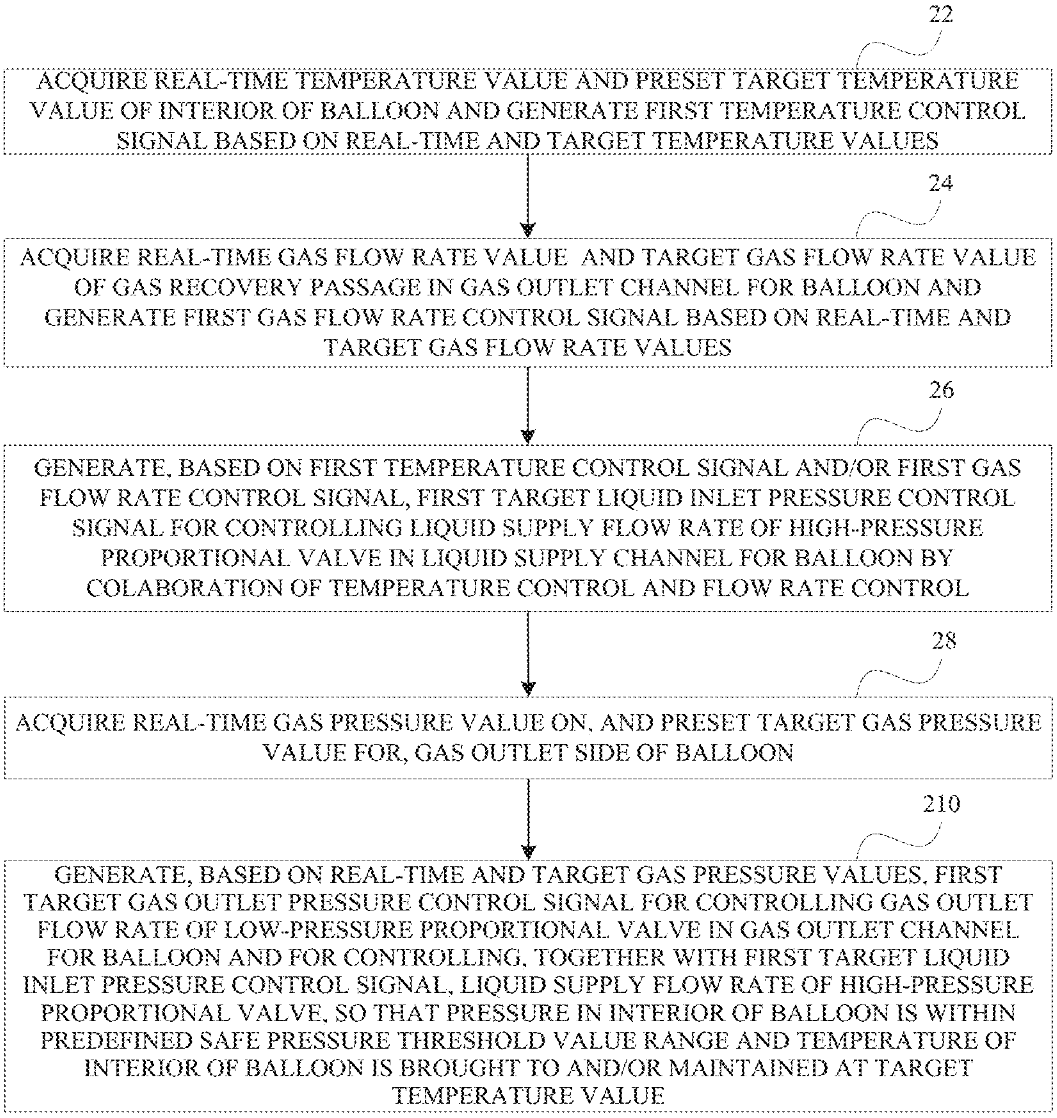
FIG. 1 shows a flowchart of a cryoablation temperature control method according to a first embodiment of the present application.

As shown in FIG. 1, in an embodiment of the present application, there is provided a cryoablation temperature control method for controlling a temperature of the interior of a cryoablation balloon. The method includes the steps as detailed below.

In Step 22, a real-time temperature value of, and a preset target temperature value for, the interior of the balloon are acquired, and a first temperature control signal is generated based on the real-time and target temperature values.

As an example, a temperature sensor may be employed to capture the real-time temperature value of the interior of the balloon, while the preset target temperature value may be set according to the requirements of a cryoablation procedure.

The first temperature control signal generated based on the real-time temperature value of the interior of the balloon and the preset target temperature value may be used to dynamically adjust a controllable parameter, e.g., a real-time flow rate value, a real-time pressure value or the like, so that a temperature of the interior of the balloon is brought to and maintained at the preset target temperature value.

In Step 24, a real-time gas flow rate value of, and a target gas flow rate value for, a gas recovery passage in a gas outlet channel for the balloon are acquired, and a first gas flow rate control signal is generated based on the real-time and target gas flow rate values.

As an example, a flow rate sensor may be employed to capture the real-time gas flow rate value of the gas recovery passage in the gas outlet channel for the balloon, while the target gas flow rate value may be input using an input device such as a touch screen or press keys. The first gas flow rate control signal generated based on the real-time and target gas flow rate values may be used to control a gas outlet flow rate of the gas recovery passage in the gas outlet channel for the balloon to the target value.

In Step 26, a first target liquid inlet pressure control signal is generated based on the first temperature control signal and/or the first gas flow rate control signal, and a liquid supply flow rate of a high-pressure proportional valve in a liquid supply channel for the balloon is controlled through collaboration of both temperature control and flow rate control.

As an example, a PID control algorithm may be employed to generate the first temperature control signal based on the target and real-time temperature values and the first gas flow rate control signal based on the real-time and target gas flow rate values. In the case of sole temperature control, the first target liquid inlet pressure control signal may be generated based on the first temperature control signal and used to dynamically adjust the liquid supply flow rate of the high-pressure proportional valve in the liquid supply channel for the balloon. In the case of sole flow rate control, the first target liquid inlet pressure control signal may be generated based on the first gas flow rate control signal and used to dynamically adjust the liquid supply flow rate of the high-pressure proportional valve in the liquid supply channel for the balloon. In the case of both temperature control and flow rate control, the first target liquid inlet pressure control signal may be generated based on both the first temperature control signal and the first gas flow rate control signal, and the liquid supply flow rate of the high-pressure proportional valve in the liquid supply channel for the balloon is dynamically adjusted through collaboration of the first temperature control signal and the first gas flow rate control signal. Alternatively, depending on the actual requirements of particular applications, the liquid supply flow rate of the high-pressure proportional valve in the liquid supply channel for the balloon may be controlled in a dynamically collaborative way with seamless switching between flow rate control and temperature control.

In Step 28, a real-time gas pressure value on, and a preset target gas pressure value for, a gas outlet side of the balloon are acquired.

As an example, a first pressure sensor may be employed to capture the real-time gas pressure value on the gas outlet side of the balloon, while the preset target gas pressure value may be input using an input device such as a touch screen or press keys.

In Step 210, based on the real-time and target gas pressure values, a first target gas outlet pressure control signal is generated for controlling a gas outlet flow rate of a low-pressure proportional valve in the gas outlet channel for the balloon and for controlling, together with the first target liquid inlet pressure control signal, the liquid supply flow rate of the high-pressure proportional valve, so that a pressure in the interior of the balloon is within a predefined safe pressure threshold value range and the temperature of the interior of the balloon is brought to and/or maintained at the target temperature value.

As an example, a PID control algorithm may be employed to control the gas outlet flow rate of the low-pressure proportional valve in the gas outlet channel for the balloon so that the pressure in the interior of the balloon is maintained within the safe pressure range. In addition, the liquid supply flow rate of the high-pressure proportional valve may be controlled in a dynamically collaborative way so that the temperature of the interior of the balloon is brought to and/or maintained at the target temperature value.

According to this embodiment, either or both of temperature control and flow rate control can be conducted based on the acquired real-time temperature value of, and target temperature value for, the interior of the cryoablation balloon and, as well as on the acquired real-time gas flow rate value of, and target gas flow rate value for, the gas recovery passage in the gas outlet channel for the balloon. In this way, seamless switching between temperature control and flow rate control is achieved, which allows dynamically collaborative control of the liquid supply flow rate of the high-pressure proportional valve in the liquid supply channel for the balloon, and of the gas outlet flow rate of the low-pressure proportional valve in the gas outlet channel for the balloon further based on the acquired real-time gas pressure value on, and the preset target gas pressure value for, the gas outlet side of the balloon. As a result, the temperature of the interior of the balloon can be brought to and maintained at the preset target temperature value, resulting in improved PVI effects. The collaboration of temperature control and flow rate control reduces operational complexity, required procedure time and surgical risk. The preset target gas pressure value, to which the gas pressure value on the gas outlet side of the balloon is brought, and at which this value is maintained, by dynamically controlling the gas outlet flow rate of the low-pressure proportional valve, keeps the pressure in the interior of the balloon above the ambient atmospheric pressure and below a relief pressure for the balloon, avoiding the risk of tearing of the tissue against which the balloon is pressed due to a too low pressure in the interior of the balloon and the risk of bursting of the balloon due to a too high pressure in the interior of the balloon. Compared with traditional systems or apparatuses that simply rely on temperature control, this application provides a user with options for flow rate control, temperature control and combined temperature and flow rate control and with seamless switching between temperature control and flow rate control. Thus, the inventive product has improved utility and increased convenience of use by allowing the user to choose a suitable control method for a particular surgical procedure. With this application, flow rate control and temperature control can be conducted in a dynamically collaborative manner, which can reduce the required procedure time and operational complexity, keep the pressure in the interior of the balloon within the predefined safe pressure threshold value range, and bring the temperature of the interior of the balloon to, and/or maintain it, at the target temperature value. Apart from this, in addition to faster and more accurate temperature control within a wider range, the balloon's interior pressure can be maintained at a proper value that avoids the risk of tearing of the tissue against which the balloon is pressed due to a too low pressure and the risk of bursting of the balloon due to a too high pressure. Thus, the balloon can operate more stably to result in improved PVI effects and reduced risk and side effects associated with the cryoablation procedure in which the balloon is used.

Figure 2:
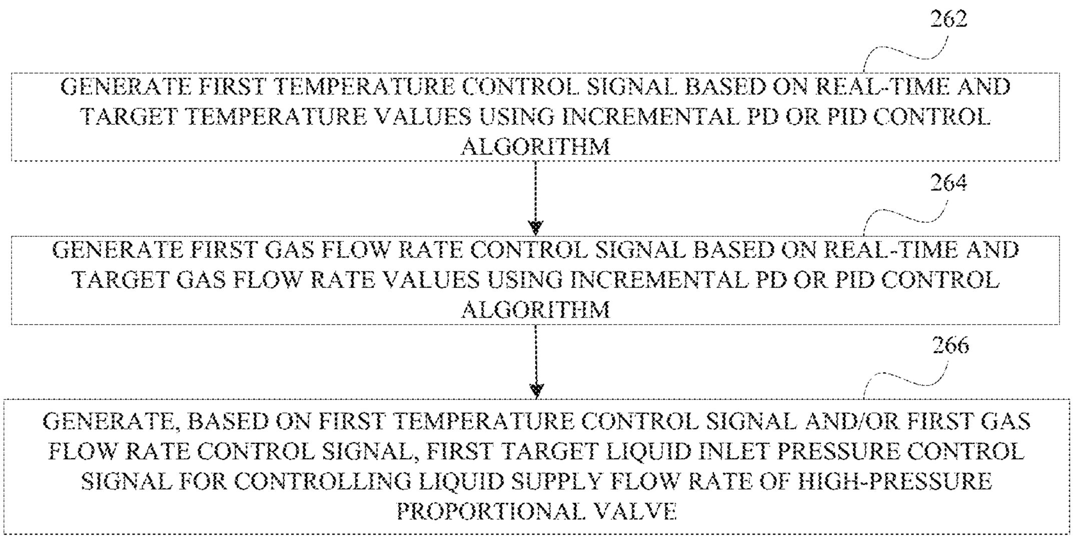
FIG. 2 shows a flowchart of a cryoablation temperature control method according to a second embodiment of the present application.

Additionally, according to an embodiment of the present application, as shown in FIG. 2, generating, based on the real-time and target temperature values and the real-time and target gas flow rate values, the first target liquid inlet pressure control signal for controlling the liquid supply flow rate of the high-pressure proportional valve in the liquid supply channel for the balloon further includes the steps of:

step 262: generating the first temperature control signal based on the real-time and target temperature values using an incremental proportional-derivative (PD) or proportional-integral-derivative (PID) control algorithm;

step 264: generating the first gas flow rate control signal based on the real-time and target gas flow rate values using an incremental PD or PID control algorithm; and step 266: generating, based on the first temperature control signal and/or the first gas flow rate control signal, the first target liquid inlet pressure control signal for controlling the liquid supply flow rate of the high-pressure proportional valve.

Figure 3:
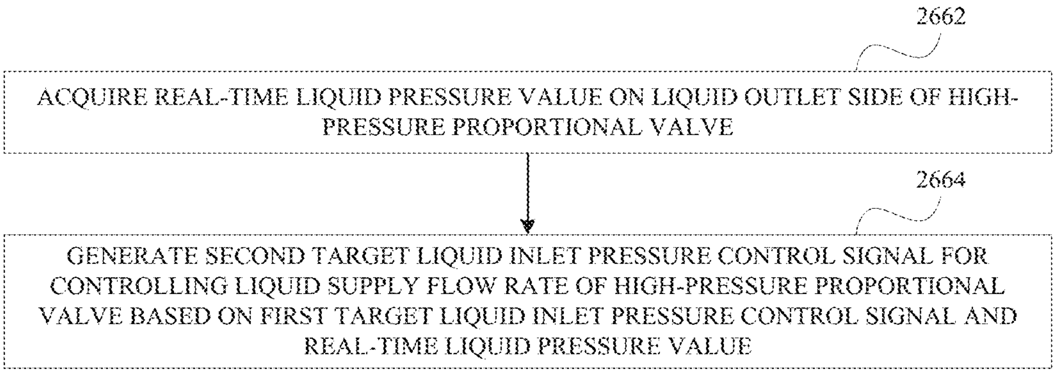
FIG. 3 shows a flowchart of a cryoablation temperature control method according to a third embodiment of the present application.

Additionally, according to an embodiment of the present application, as shown in FIG. 3, controlling the liquid supply flow rate of the high-pressure proportional valve further includes the steps of:

step 2662: acquiring a real-time liquid pressure value on a liquid outlet side of the high-pressure proportional valve; and step 2664: generating a second target liquid inlet pressure control signal for controlling the liquid supply flow rate of the high-pressure proportional valve based on the first target liquid inlet pressure control signal and the real-time liquid pressure value.

According to this embodiment, the temperature of the interior of the balloon is brought to and/or maintained at the target temperature value by dynamically controlling the liquid supply flow rate of the high-pressure proportional valve based on the second target liquid inlet pressure control signal generated from the real-time liquid pressure value acquired on the liquid outlet side of the high-pressure proportional valve arranged on a liquid supply side of the balloon and a target value indicated in the first target liquid inlet pressure control signal. The cryoablation temperature control based on the dynamical control of the liquid supply flow rate of the high-pressure proportional valve based on the second target liquid inlet pressure control signal generated from the real-time liquid pressure value on the liquid outlet side of the high-pressure proportional valve and from the first target liquid inlet pressure control signal is accomplished by either or both of flow rate control and temperature control. In this way, seamless switching between flow rate control and temperature control is achieved. In the current practice, physicians are used to flow rate control, which, however, leads to a continual decrease in temperature. In the absence of temperature control that allows the temperature to be maintained at a desired value, the ablation process has to be interrupted optionally for several times, possibly leading to a prolonged time of the balloon staying within the patient's body. Therefore, the coordinated use of, and thus seamless switching between, flow rate control and temperature control according to this embodiment can result in a significant reduction in the required procedure time.

Figure 4:
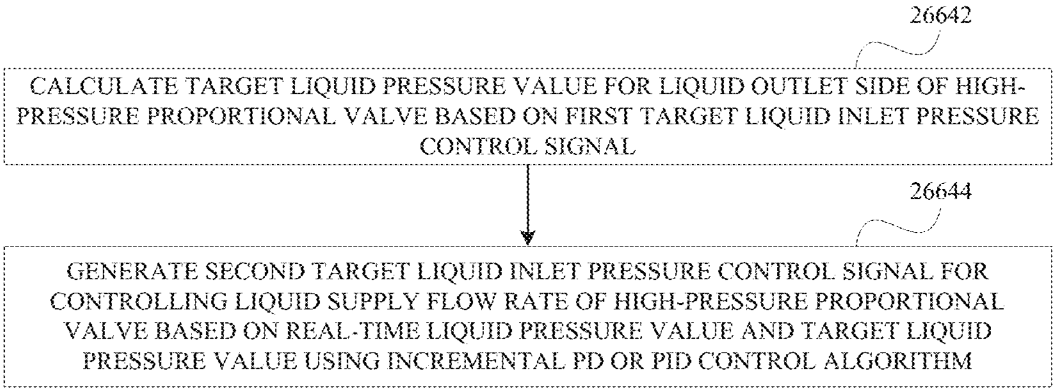
FIG. 4 shows a flowchart of a cryoablation temperature control method according to a fourth embodiment of the present application.

Additionally, according to an embodiment of the present application, as shown in FIG. 4, controlling the liquid supply flow rate of the high-pressure proportional valve further includes the steps of:

step 26642: calculating a target liquid pressure value for the liquid outlet side of the high-pressure proportional valve based on the first target liquid inlet pressure control signal; and step 26644: generating the second target liquid inlet pressure control signal for controlling the liquid supply flow rate of the high-pressure proportional valve base on the real-time and target liquid pressure values using an incremental PD or PID control algorithm.

According to this embodiment, calculating the target liquid pressure value for the liquid outlet side of the high-pressure proportional valve based on the first target liquid inlet pressure control signal and generating the second target liquid inlet pressure control signal using an incremental PD or PID control algorithm enables seamless switching between flow rate control and temperature control and hence dynamical control of the liquid supply flow rate of the high-pressure proportional valve, which addresses both temperature control and flow rate control needs and allows the temperature of the interior of the balloon to be brought to and/or maintained at the target temperature value, with increased coordination between the multiple control parameters, reduced operational complexity and a shortened time required for the procedure.

Additionally, according to an embodiment of the present application, as shown in FIG. 5, generating the first target gas outlet pressure control signal for controlling the gas outlet flow rate of the low-pressure proportional valve in the gas outlet channel for the balloon based on the real-time and target gas pressure values includes the step of:

step 2012: generating the first target gas outlet pressure control signal based on the real-time and target gas pressure values using an incremental PD or PID control algorithm.

According to this embodiment, dynamically controlling the gas outlet flow rate of the low-pressure proportional valve using an incremental PD or PID control algorithm keeps the pressure in the interior of the balloon within the predefined safe pressure threshold value range, e.g., at a value above the ambient atmospheric pressure and below the relief pressure of the balloon, which avoids the risk of tearing of the tissue against which the balloon is pressed due to a too low pressure and the risk of bursting of the balloon due to a too high pressure.

Additionally, according to an embodiment of the present application, the method further includes the steps of:

predicting a slope of profile of real-time gas flow rate value to control the target gas flow rate value and dividing the real-time temperature profile into at least two phases including a rapid temperature drop phase and a slow temperature drop phase based on the real-time temperature value, wherein in the slow temperature drop phase, the real-time gas flow rate value is maintained in a predefined stable flow rate threshold value range.

Dividing the balloon temperature profile at least into the rapidly and slow temperature drop phases and adopting respective suitable control strategies in these phases allows more accurate temperature control with improved efficiency and no flow rate fluctuations.

Additionally, according to an embodiment of the present application, as shown in FIG. 6, generating, based on the real-time and target gas pressure values, the first target gas outlet pressure control signal for controlling the gas outlet flow rate of the low-pressure proportional valve in the gas outlet channel for the balloon so that the temperature of the interior of the balloon is brought to and/or maintained at the target temperature value further includes the step of:

step 2013: with the real-time gas flow rate value being in the predefined stable flow rate threshold value range, linearly incrementing an opening of the low-pressure proportional valve and, upon the low-pressure proportional valve being fully open, activating a solenoid valve in the gas outlet channel for the balloon so that at least a part of gas discharged from the balloon passes through the solenoid valve and then flows into the gas recovery passage.

According to this embodiment, temperature and/or flow rate control of the balloon may begin with causing a rapid drop in the temperature of the interior of the balloon, and when the detected real-time gas flow rate value drops into the predefined stable flow rate threshold value range, i.e., the slow temperature drop phase (in this phase, the real-time gas flow rate value may be controlled to be within the stable flow rate threshold value range), the opening of the low-pressure proportional valve may be linearly incremented. When the low-pressure proportional valve is fully open, the solenoid valve in the gas outlet channel for the balloon may be activated to switch to a mode in which the solenoid valve is controlled to allow the temperature of the interior of the balloon to slowly drop to the preset target temperature value. This allows more stable flow rate transitioning without abrupt fluctuations.

Additionally, according to an embodiment of the present application, when the low-pressure proportional valve is fully open, the low-pressure proportional valve is deactivated simultaneously with the activation of the solenoid valve in the gas outlet channel for the balloon so that a gas is discharged from the balloon entirely flowing through the solenoid valve into the gas recovery passage, resulting in the pressure in the interior of the balloon dropping into the predefined safe pressure threshold value range and the temperature of the interior of the balloon being brought to and/or maintained at the target temperature value. Experiments have shown that this control approach featured more stable variation of temperature without flow rate fluctuations during the slow temperature drop phase.

Additionally, according to an embodiment of the present application, as shown in FIG. 7, generating, based on the real-time and target gas pressure values, the first target gas outlet pressure control signal for controlling the gas outlet flow rate of the low-pressure proportional valve in the gas outlet channel for the balloon further includes the step of:

step 2014: upon the real-time gas flow rate value falling below a predefined flow rate threshold value range, increasing an opening of the high-pressure proportional valve so that the pressure in the interior of the balloon is brought back into the predefined safe pressure threshold range.

According to this embodiment, whenever the real-time gas flow rate value drops below the predefined flow rate threshold value range, the pressure in the interior of the balloon is increased and brought back into the safe pressure threshold range to protect the balloon from shrinking so as to avoid tearing of the tissue against which the balloon is pressed due to excessive shrinkage of the balloon in the course of cryoablation. In this way, both stable supply and discharge flow rates can be ensured for the balloon while keeping the pressure in the interior of the balloon within the safe pressure threshold range.

Additionally, according to an embodiment of the present application, as shown in FIG. 8, the method further includes the step of:

step 2016: upon the real-time temperature value of the interior of the balloon becoming less than or equal to a preset temperature threshold value, bringing it back to the preset target temperature value through reducing the opening of the high-pressure proportional valve and/or adjusting the opening of the low-pressure proportional valve.

According to this embodiment, when the real-time temperature value of the interior of the balloon is less than or equal to the preset temperature threshold value, the high-pressure proportional valve and/or low-pressure proportional valve is/are switched to a rewarming/protection mode to avoid causing damage to the tissue due to a too low temperature.

It is to be understood that although the steps in each of the processes in the flowcharts of FIGS. 1 to 8 are shown in sequential order as indicated by the arrows, they are not necessarily performed in that order. These steps are not limited to being performed strictly in any particular order and may be performed in any other suitable order than that shown in the figure. Moreover, at least some of the steps shown in FIGS. 1 to 8 may include multiple sub-steps or phases, which are not necessarily performed at the same time and may be performed at different times. In addition, these sub-steps or phases are not necessarily performed in any particular order. Rather, they may be performed alternately with other steps or at least some sub-steps or phases thereof.

Figure 9:
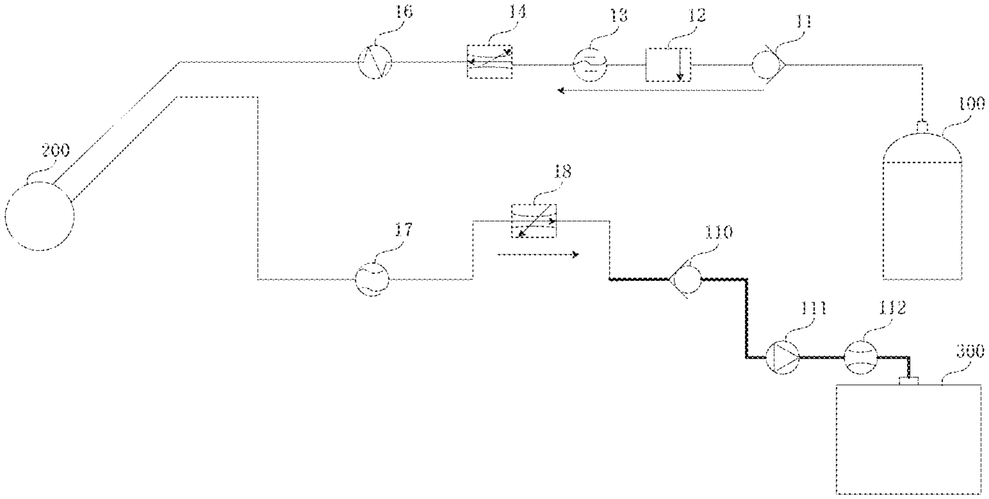
FIG. 9 shows a schematic illustrating the architecture of a cryoablation temperature control system according to a ninth embodiment of the present application.
Figure 10:
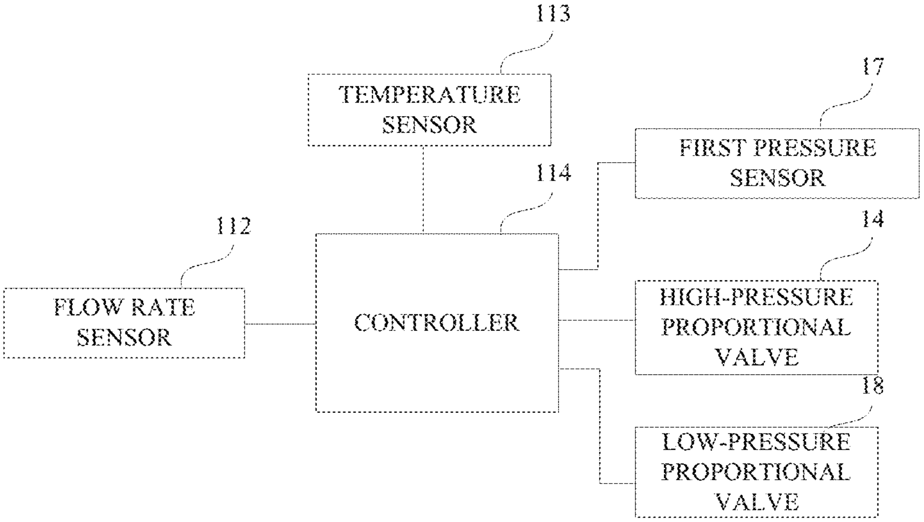
FIG. 10 shows a schematic illustrating the control system architecture of a cryoablation temperature control system according to a tenth embodiment of the present application.

According to an embodiment of the present application, there is provided a cryoablation temperature control system for controlling a temperature of the interior of a cryoablation balloon 200. As shown in FIGS. 9 to 10, the system includes: a temperature sensor 113 for capturing a real-time temperature value of the interior of the cryoablation balloon 200; a high-pressure proportional valve 14 disposed in a liquid supply channel for the balloon 200; a first pressure sensor 17 disposed in a gas outlet channel for the balloon 200 and configured to capture a real-time gas pressure value on a gas outlet side of the balloon 200; a low-pressure proportional valve 18 disposed in the gas outlet channel for the balloon 200 and configured to adjust the pressure of a gas in the interior of the balloon; a flow rate sensor 112 disposed in the gas outlet channel for the balloon 200 and configured to capture a real-time gas flow rate value of a gas recovery passage in the gas outlet channel for the balloon 200; and a controller 114 coupled to each of the temperature sensor 113, the high-pressure proportional valve 14, the first pressure sensor 17, the low-pressure proportional valve 18 and the flow rate sensor 112.

Specifically, the controller 114 may be configured to:

acquire the real-time temperature value of, and a preset target temperature value for, the interior of the cryoablation balloon 200, generate a first temperature control signal based on the real-time and target temperature values, acquire the real-time gas flow rate value of, and a target gas flow rate value for, the gas recovery passage in the gas outlet channel for the balloon, generate a first gas flow rate control signal based on the real-time and target gas flow rate values, and generate, based on the first temperature control signal and/or the first gas flow rate control signal, a first target liquid inlet pressure control signal for controlling a liquid supply flow rate of the high-pressure proportional valve 14 in the liquid supply channel for the balloon 200 through collaboration of both temperature control and flow rate control; and acquire a real-time gas pressure value on, and a preset target gas pressure value for, the gas outlet side of the balloon 200 and generate, based on the real-time and target gas pressure values, a first target gas outlet pressure control signal for controlling a gas outlet flow rate of the low-pressure proportional valve 18 and for controlling, together with the first target liquid inlet pressure control signal, the liquid supply flow rate of the high-pressure proportional valve 14, so that a pressure in the interior of the cryoablation balloon 200 is within a predefined safe pressure threshold value range and the temperature of the interior of the cryoablation balloon 200 is brought to and/or maintained at the target temperature value.

For example, as shown in FIG. 9, the system may further include: a first check valve 11, a pressure relief valve 12, a pressure gauge 13 and a compressor 16, which are arranged in the liquid supply channel; and the low-pressure proportional valve 18, a second check valve 110 and a vacuum pump 111, which are arranged in the gas outlet channel. A cryogenic liquid from a reservoir 100 may flow sequentially through the first check valve 11, the pressure relief valve 12, the pressure gauge 13, the high-pressure proportional valve 14 and the compressor 16 into the balloon 200, where it may absorb heat and evaporate into a gas, which may then flow sequentially through the first pressure sensor 17, the low-pressure proportional valve 18, the second check valve 110, the vacuum pump 111 and the flow rate sensor 112 into a return gas storage device 300.

In the system according to this embodiment, the controller 114 can perform either or both of temperature control and flow rate control based on the acquired real-time temperature value of, and target temperature value for, the interior of the cryoablation balloon 200 and, as well as on the acquired real-time gas flow rate value of, and target gas flow rate value for, the gas recovery passage in the gas outlet channel for the balloon. In this way, seamless switching between temperature control and flow rate control is achieved, which allows dynamically collaborative control of the liquid supply flow rate of the high-pressure proportional valve 14 in the liquid supply channel for the balloon 200, and of the gas outlet flow rate of the low-pressure proportional valve 18 in the gas outlet channel for the balloon 200 further based on the acquired real-time gas pressure value on, and the preset target gas pressure value for, the gas outlet side of the balloon 200. As a result, the temperature of the interior of the balloon 200 can be brought to and maintained at the preset target temperature value, resulting in improved PVI effects and reduced operational complexity, required procedure time and surgical risk. The preset target gas pressure value, to which the gas pressure value on the gas outlet side of the balloon is brought, and at which this value is maintained, by dynamically controlling the gas outlet flow rate of the low-pressure proportional valve 18, keeps the pressure in the interior of the balloon above the ambient atmospheric pressure and below a relief pressure for the balloon 200, avoiding the risk of tearing of the tissue against which the balloon is pressed due to a too low pressure in the interior of the balloon and the risk of bursting of the balloon due to a too high pressure in the interior of the balloon.

Additionally, according to an embodiment of the present application, as shown in FIG. 10, the controller 114 is configured to:

generate the first temperature control signal based on the real-time and target temperature values using an incremental proportional-derivative (PD) or proportional-integral-derivative (PID) control algorithm;

generate the first gas flow rate control signal based on the real-time and target gas flow rate values using an incremental PD or PID control algorithm;

generate, based on the first temperature control signal and/or the first gas flow rate control signal, the first target liquid inlet pressure control signal for controlling the liquid supply flow rate of the high-pressure proportional valve; and acquire the real-time gas pressure value on, and the preset target gas pressure value for, the gas outlet side of the balloon and generate, based on the real-time and target gas pressure values, the first target gas outlet pressure control signal for controlling the gas outlet flow rate of the low-pressure proportional valve using an incremental PD or PID control algorithm.

Figure 11:
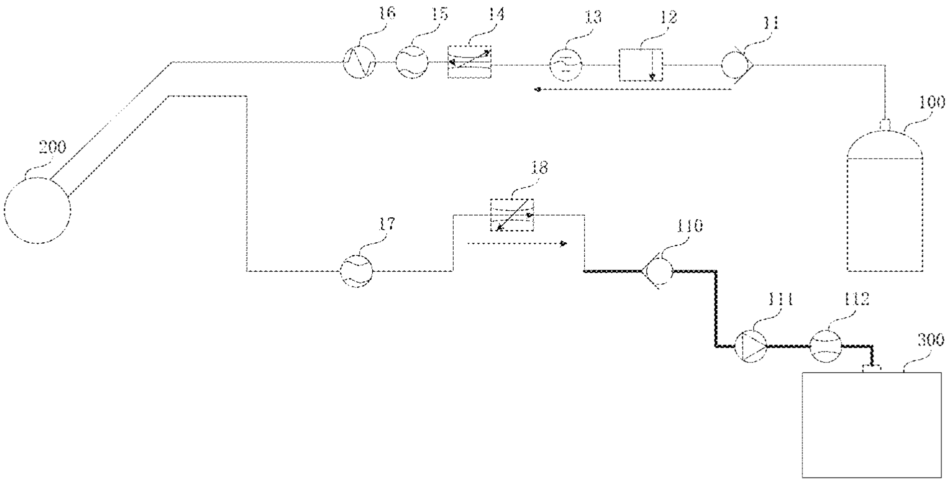
FIG. 11 shows a schematic illustrating the architecture of a cryoablation temperature control system according to an eleventh embodiment of the present application.
Figure 12:
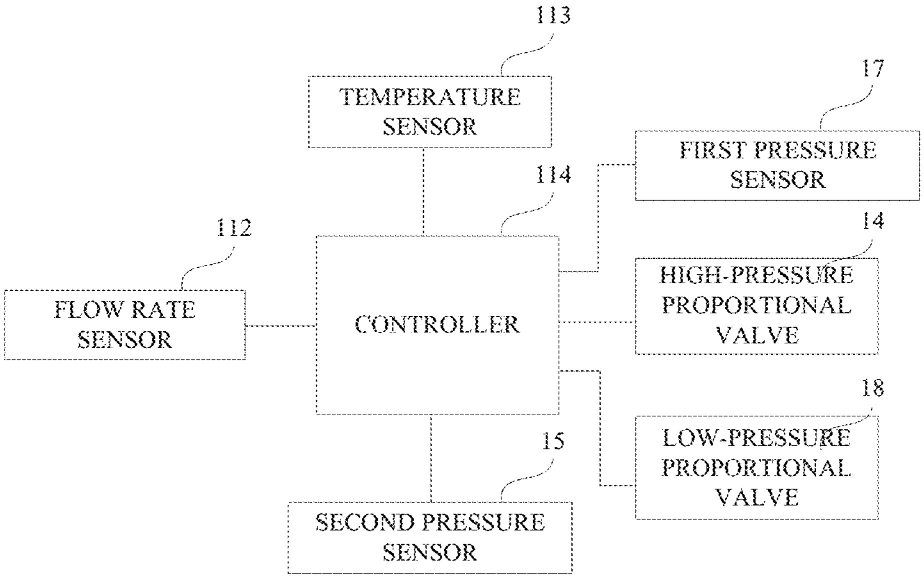
FIG. 12 shows a schematic illustrating the control system architecture of a cryoablation temperature control system according to a twelfth embodiment of the present application.

Additionally, according to an embodiment of the present application, as shown in FIGS. 11 to 12, the system further includes a second pressure sensor 15 in the liquid inlet channel for the balloon 200, which is coupled to the controller 114 and configured to capture a real-time liquid pressure value on a liquid outlet side of the high-pressure proportional valve 14. Additionally, the controller 114 is further configured to acquire the real-time liquid pressure value and generate, based on the first target liquid inlet pressure control signal and the real-time liquid pressure value, a second target liquid inlet pressure control signal for controlling the liquid supply flow rate of the high-pressure proportional valve.

According to this embodiment, the controller 114 dynamically controls the liquid supply flow rate of the high-pressure proportional valve 14 based on the acquired real-time liquid pressure value on the liquid outlet side of the high-pressure proportional valve 14 arranged on the liquid supply side of the balloon 200 and on a target value indicated in the first target liquid inlet pressure control signal, thereby bringing the temperature of the interior of the cryoablation balloon 200 to and/or maintaining it at the target temperature value.

Figure 13:
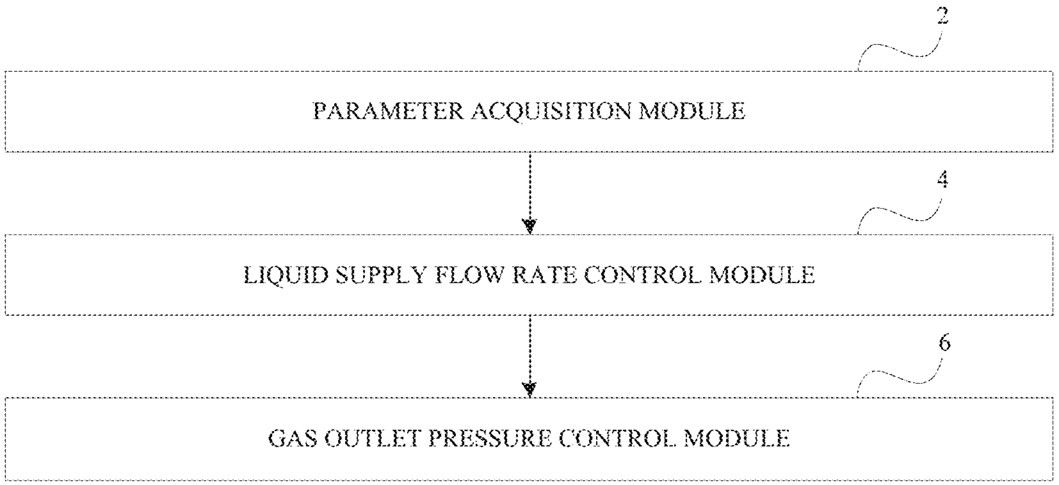
FIG. 13 schematically illustrates an arrangement of modules in a controller of a cryoablation temperature control system according to a thirteenth embodiment of the present application.

According to an embodiment of the present application, there is provided a cryoablation temperature control system for controlling a temperature of the interior of a cryoablation balloon. As shown in FIG. 13, the system includes: a parameter acquisition module 2 configured to acquire a real-time temperature value of, and a preset target temperature value, for the interior of the balloon, a real-time gas flow rate value of, and a target gas flow rate value for, a gas recovery passage in a gas outlet channel for the balloon, and a real-time gas pressure value on, and a preset target gas pressure value for, a gas outlet side of the balloon; a liquid supply flow rate control module 4 configured to generate a first temperature control signal based on the real-time and target temperature values, generate a first gas flow rate control signal based on the real-time and target gas flow rate values, and generate, based on the first temperature control signal and/or the first gas flow rate control signal, a first target liquid inlet pressure control signal for controlling a liquid supply flow rate of a high-pressure proportional valve in a liquid supply channel for the balloon by means of both temperature control and flow rate control; and a gas outlet pressure control module 6 configured to generate, based on the real-time and target gas pressure values, a first target gas outlet pressure control signal for controlling a gas outlet flow rate of a low-pressure proportional valve in the gas outlet channel for the balloon. The liquid supply flow rate control module 4 and the gas outlet pressure control module 6 coordinate with each other to perform control so that a pressure in the interior of the balloon is within a predefined safe pressure threshold value range and the temperature of the interior of the balloon is brought to and/or maintained at the target temperature value. In one embodiment, the parameter acquisition module may be implemented as a digital-to-analog converter, while the liquid supply flow rate control module and the gas outlet pressure control module may be implemented as separate PID controllers.

Figure 14:
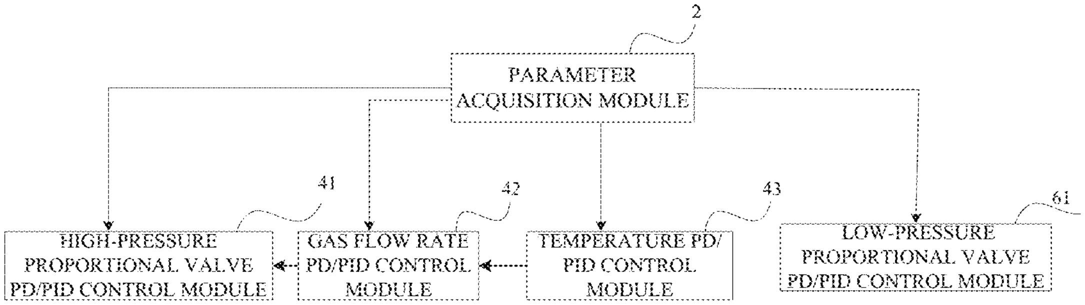
FIG. 14 schematically illustrates an arrangement of modules in a controller of a cryoablation temperature control system according to a fourteenth embodiment of the present application.

Additionally, according to an embodiment of the present application, as shown in FIG. 14, the parameter acquisition module 2 may be further configured to acquire a real-time liquid pressure value on a liquid outlet side of the high-pressure proportional valve. The liquid supply flow rate control module may include: a temperature PD/PID control module 43 for generating the first temperature control signal based on the real-time and target temperature values using an incremental PD or PID control algorithm; a gas flow rate PD/PID control module 42 for generating the first gas flow rate control signal based on the real-time and target gas flow rate values using an incremental PD or PID control algorithm; and a high-pressure proportional valve PD/PID control module 41 for generating the first target liquid inlet pressure control signal based on the first temperature control signal and/or the first gas flow rate control signal, calculating a target liquid pressure value for the liquid outlet side of the high-pressure proportional valve based on the first target liquid inlet pressure control signal and generating, based on the real-time and target liquid pressure values using an incremental PD or PID control algorithm, a second target liquid inlet pressure control signal for controlling the liquid supply flow rate of the high-pressure proportional valve. The gas outlet pressure control module may include a low-pressure proportional valve PD/PID control module 61 for generating, based on the real-time and target gas pressure values using an incremental PD or PID control algorithm, the first target gas outlet pressure control signal for controlling the gas outlet flow rate of the low-pressure proportional valve. The temperature PD/PID control module, gas flow rate PD/PID control module, high-pressure proportional valve PD/PID control module and low-pressure proportional valve PD/PID control module may coordinate with one another to perform control so that the pressure in the interior of the balloon is within the predefined safe pressure threshold value range and the temperature of the interior of the balloon is brought to and/or maintained at the target temperature value. In other words, the controller 114 control the first temperature control signal, first gas flow rate control signal, second target liquid inlet pressure control signal and/or first target gas outlet pressure control signal in a coordinated way so that the pressure in the interior of the balloon is within the predefined safe pressure threshold value range and the temperature of the interior of the balloon is brought to and/or maintained at the target temperature value. In one embodiment, the temperature PD/PID control module, gas flow rate PD/PID control module, high-pressure proportional valve PD/PID control module and low-pressure proportional valve PD/PID control module may be implemented as separate PID controllers.

As an example, dynamically controlling the temperature of the interior of the balloon value to the preset temperature value by the temperature PD/PID control module using an incremental PD or PID control algorithm allows a rapid decrease in temperature and differential prediction of how the liquid supply flow rate rises, avoiding overshoot of liquid supply flow rate. Dynamically controlling the gas flow rate on the gas outlet side of the balloon by the gas flow rate PD/PID control module using an incremental PD or PID control algorithm allow dividing the gas flow rate profile into a number of segments, for each of which, predicting a slope of a profile of the real-time gas flow rate value to control the target gas low rate to rise gradually. This results in more accurate gas flow rate control and more stable maintenance of the flow rate on the gas outlet side of the balloon at the preset target value. By bringing the gas pressure on the gas outlet side of the balloon to, and maintaining it at, the preset target gas pressure value through dynamically controlling the gas outlet flow rate of the low-pressure proportional valve using an incremental PD or PID control algorithm, the pressure in the interior of the balloon can be maintained at a value above the ambient atmospheric pressure and below a relief pressure of the balloon, which avoids the risk of tearing of the tissue against which the balloon is pressed due to a too low pressure and the risk of bursting of the balloon due to a too high pressure.

According to this embodiment, the coordinated control accomplished by the four modules, i.e., the temperature PD/PID control module, the gas flow rate PD/PID control module, the high-pressure proportional valve PD/PID control module and the low-pressure proportional valve PD/PID control module, allows a user to choose from sole flow rate control, sole temperature control and combined temperature and flow rate control according to his/her own application and provides him/her with seamless switching between temperature control and flow rate control. In addition to easier operational complexity and faster and more accurate temperature control within a wider range, this enables the balloon's interior pressure to be maintained at a proper value that avoids the risk of tearing of the tissue against which the balloon is pressed due to a too low pressure and the risk of bursting of the balloon due to a too high pressure. Thus, the balloon can operate more stably to result in improved PVI effects and reduced risk and side effects associated with the cryoablation procedure in which the balloon is used.

Reference may be made to the above description of the method for further details of the system, so that a repeated description is not necessary.

Figure 15:
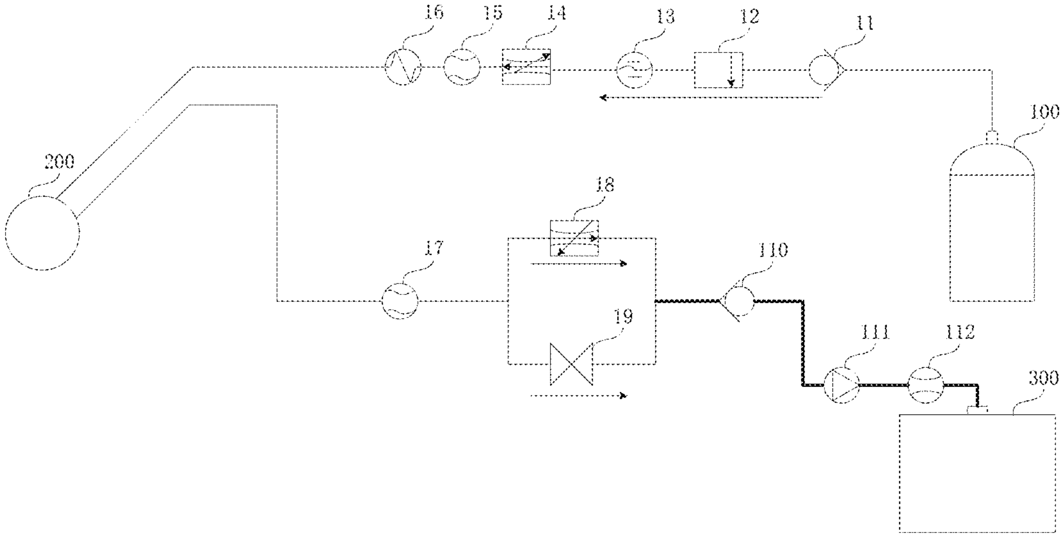
FIG. 15 shows a schematic illustrating the architecture of a cryoablation temperature control system according to a fifteenth embodiment of the present application.
Figure 16:
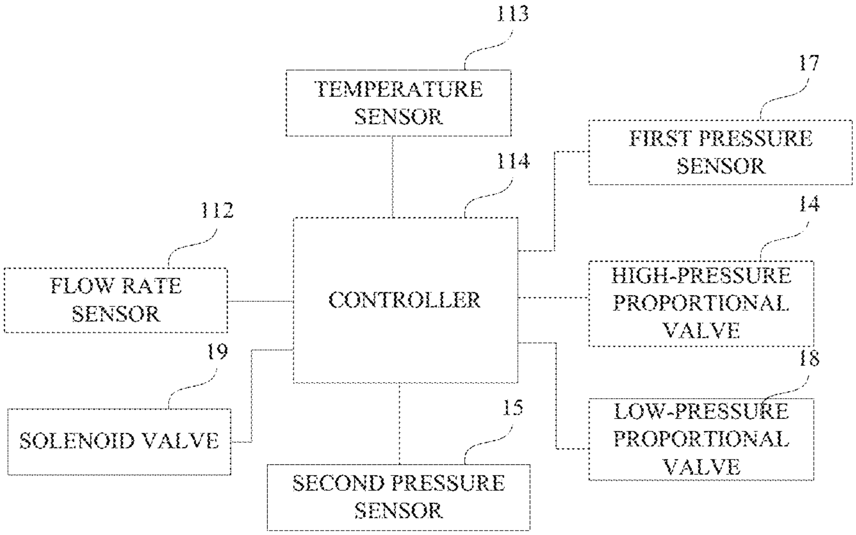
FIG. 16 shows a schematic illustrating the control system architecture of a cryoablation temperature control system according to a sixteenth embodiment of the present application.

Additionally, according to an embodiment of the present application, as shown in FIGS. 15 to 16, the system further includes a solenoid valve 19, which is disposed in the gas outlet channel for the balloon 200 in parallel with the low-pressure proportional valve and configured for the passage therethrough of a gas discharged from the balloon 200 into the gas recovery passage.

Specifically, in a slow temperature drop phase, when the real-time gas flow rate value is within a predefined stable flow rate threshold value range, under the control of the controller 114, an opening of the low-pressure proportional valve 18 may be linearly incremented, and upon the low-pressure proportional valve 18 being fully open, the solenoid valve 19 in the gas outlet channel for the balloon 200 may be activated, with the low-pressure proportional valve 18 being simultaneously deactivated. Compared with traditional approaches in which only a low-pressure proportional valve is employed and maintained at a certain flow rate, the coordinated control of the solenoid valve 19 and the low-pressure proportional valve 18 according to this embodiment allows the pressure in the interior of the balloon value to be kept in the predefined safe pressure threshold value range, resulting in good temperature control without fluctuations or overshoot of flow rate. As a result, significantly improved temperature control accuracy of up to ±1 degree can be achieved. When the real-time gas flow rate value drops below a predefined flow rate threshold value range, under the control of the controller 114, an opening of the high-pressure proportional valve 14 may be increased to bring the pressure in the interior of the balloon back into the predefined safe pressure threshold value range.

In alternative embodiments, it is also possible for the controller 114 to activate the solenoid valve 19 in the gas outlet channel for the balloon 200 while not deactivating the low-pressure proportional valve 18 so that the solenoid valve 19 and the low-pressure proportional valve 18 both operate to allow at least a part of the gas from the balloon to pass through the solenoid valve 19. However, the present invention is not so limited.

Additionally, according to an embodiment of the present application, the controller is further configured to:

when the real-time temperature value of the interior of the balloon becomes less than or equal to a preset temperature threshold value, activate a rewarming/protection mode by reducing the opening of the high-pressure proportional valve and/or adjusting the opening of the low-pressure proportional valve so that the real-time temperature value of the interior of the balloon is brought to the preset target temperature value without causing unnecessary damage to the tissue due to an excessively low temperature.

Figure 17:
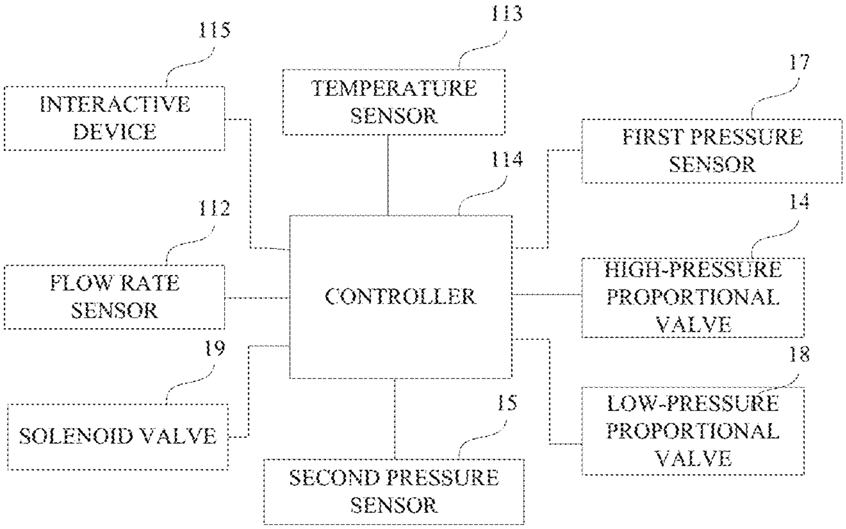
FIG. 17 shows a schematic illustrating the control system architecture of a cryoablation temperature control system according to a seventeenth embodiment of the present application.

Additionally, according to an embodiment of the present application, as shown in FIG. 17, the cryoablation temperature control system further includes an interactive device 115 coupled to the controller 114, which is configured for input of the aforementioned target temperature or gas flow rate values.

According to this embodiment, the interactive device 115 coupled to the controller 114 allows a user to input the target temperature or gas flow rate values, which are used in combined temperature and flow rate control for bringing the temperature of the interior of the balloon to and/or maintaining it at the target temperature value. As a result, seamless switching between flow rate control and temperature control is achieved, resulting in easier operation of a physician, a significantly reduced procedure time, lower operational complexity and improved PVI effects.

As an example, the interactive device 115 may include at least one of a keyboard, a touch screen, a touch display screen, press keys or a voice input device.

Additionally, according to an embodiment of the present application, the temperature sensor, the first pressure sensor, the second pressure sensor and the flow rate sensor in the cryoablation temperature control system may be coupled to the controller via respective analog-to-digital converter circuits, and the controller may generate, based on the real-time temperature value of the interior of the balloon captured by the temperature sensor, the real-time gas flow rate value of the gas recovery passage captured by the first pressure sensor, and the preset target temperature and gas flow rate values input through the interactive device, the first target liquid inlet pressure control signal, which may be then passed through a first digital-to-analog converter circuit and a first amplifier circuit to a driver circuit for the high-pressure proportional valve so as to control the liquid supply flow rate of the high-pressure proportional valve. Additionally, the controller may generate, based on the real-time and target gas pressure values, the first target gas outlet pressure control signal, which may be then passed through a second digital-to-analog converter circuit and a second amplifier circuit to a driver circuit for the low-pressure proportional valve so as to control the gas outlet flow rate of the low-pressure proportional valve. Under the control of the controller, the interactive device may display in real time the real-time temperature value captured by the temperature sensor, the real-time gas flow rate value of the liquid outlet side of the balloon captured by the first pressure sensor, the real-time pressure value on the liquid outlet side of the high-pressure proportional valve captured by the second pressure sensor and the real-time gas flow rate value of the gas recovery passage captured by the flow rate sensor. In a cryoablation process, a user may provide the preset target temperature value and/or the target flow rate value via the interactive device such as a touch screen, and the controller may perform PID calculations based on the acquired data. The resulting digital signals may be converted by the respective digital-to-analog converter circuits to analog signals, which may be then amplified by the respective amplifiers. The amplified signals may be fed to the respective driver circuits to control, in a dynamically collaborative way, the openings of the high- and low-pressure proportional valves and actions of the solenoid valve so that the temperature of the interior of the balloon is brought to the target temperature value and the pressure in the interior of the balloon is maintained within the predefined safe pressure threshold value range, thus avoiding the risk of tearing of the tissue against which the balloon is pressed due to a too low pressure and the risk of bursting of the balloon due to a too high pressure.

Figure 18:
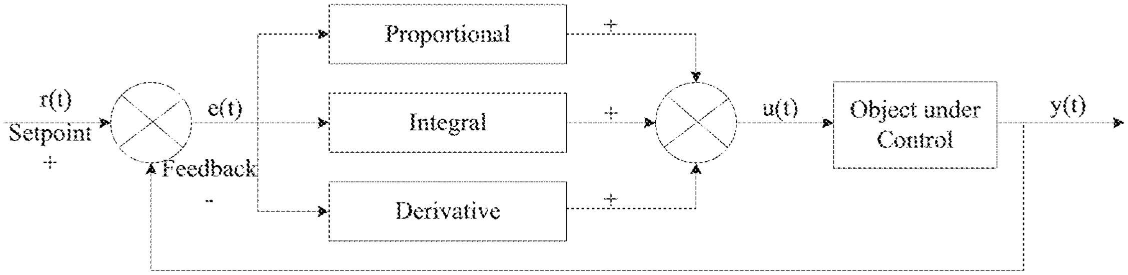
FIG. 18 is a schematic diagram of PID control according to embodiments of the present application.

Specifically, in FIG. 18, a diagram of PID control, r(t) denotes a preset target value; y(t) denotes an actual output value of the system; and e(t) denotes a control error as the difference between the preset target value and the actual output value, i.e., e(t)=r(t)−y(t). When e(t) is fed to the PID controller, u(t) is an output of the PID and an input for the quantity under control.

Proportional (P) control features fast response to errors and is in particular effective for large errors, but cannot get rid of a stable-state error. A high proportional constant would cause the system to be unstable. Integral (I) control functions to accumulate any error in the system and output a control quantity to cancel out the accumulated error. Given enough time, integral control can effectuate elimination of any error, including the stable-state error. However, an excessively large integral gain may cause a significant amount of system overshoot, or even oscillation of the system. Derivative (D) control can mitigate overshoot, overcome oscillation, increase system stability and speed up dynamic response of the system, thus improving its dynamical performance. Depending on the characteristics of an object under control, PID control may be simplified as P, PI or PD control. For temperature control, the PD and PID modes are most commonly used.

From the diagram of PID control, we can obtain the following approximate equation:

$$u(t) = K_p\left[e(t) + \frac{1}{T_I}\int_0^t e(t)dt + T_D\frac{de(t)}{dt}\right] + u_0, \quad (1\text{-}1)$$

where u(t) represents a PID control output signal; e(t) represents the difference between a preset target value and an actual output value; $K_p$ represents a proportional constant; $T_I$ represents an integral action time; $T_D$, a derivative action time; $u_0$, a control constant; and t, a time constant. Eqn. 1-1 may be discretized through substituting the integral term with a summation term, and the derivative term with an incremental term:

$$t \approx kT \quad k \in [1, N] \tag{1-2}$$

$$\int_0^t e(t)dt \approx T\sum_{j=0}^{k} e_j \tag{1-3}$$

$$\frac{de(t)}{dt} \approx \frac{e_t - e_{t-1}}{T}. \tag{1-4}$$

In these equations, T represents a sampling period; each of j and k, an ordinal number of a given sample; N represents the total number of samples; t represents the time constant, which corresponds to kT, and $e_t$ and $e_{t-1}$, errors of two consecutive samples.

From Eqns. 1-2, 1-3 and 1-4, we can obtain the following discretized equation $$u_k = K_p\left[e_k + \frac{1}{T_I}\sum_{j=0}^{k} e_j + T_d\frac{e_k - e_{k-1}}{T}\right] + u_0, \tag{1-5}$$

and derive from Eqn. 1-5 the following incremental PID equation $$\Delta u_k = u_k - u_{k-1}$$

$$\begin{aligned}\Delta u_k = u_k - u_{k-1} &= K_p\left[e_k - e_{k-1} + \frac{T}{T_I}e_k + T_d\frac{e_k - 2e_{k-1} + e_{k-2}}{T}\right] \\ &= K_p\left(1 + \frac{T}{T_i} + \frac{T_d}{T}\right)e_t - K_p\left(1 + \frac{2T_d}{T}\right)e_{t-1} + K_p\frac{T_d}{T}e_{t-2}\end{aligned} \tag{1-6}$$

$$e_t = r(t) - y(t). \tag{1-7}$$

In these equations, $\Delta u_k$ denotes an increment of the control quantity; $K_p$ denotes the proportional constant; $T_i$ denotes an integral parameter; $T_d$ denotes a derivative parameter; $e_k$, $e_{k-1}$ and $e_{k-2}$ denote errors of three consecutive samples; and T denotes the sampling period. For a PID controller, a control quantity is output in response to the input of a sample. In general cases, the sampling period is taken as a control period. For temperature control and flow rate control, control periods of the proportional valves should be determined separately based on their own response characteristics and may range from 50 ms to 200 ms. A sampling period for flow rate control may be in the range of 1 s to 3 s. Due to the delayed nature of flow rate control, fast control may lead to a significant stable-state error. A control period for temperature control may range from 500 ms to 2 s.

In order to bring the temperature of the balloon to the preset target temperature value, the openings of the proportional valves may be incrementally adjusted according to Eqn. 1-6. That is, the openings may be increased or reduced in an incremental manner. Voltage signals of magnitude on the order of millivolts may be used in such control, and a higher resolution allows more accurate control of the openings and more stable flow rates thereof. In this way, the balloon temperature can be eventually tuned to the preset target temperature.

Figure 19:
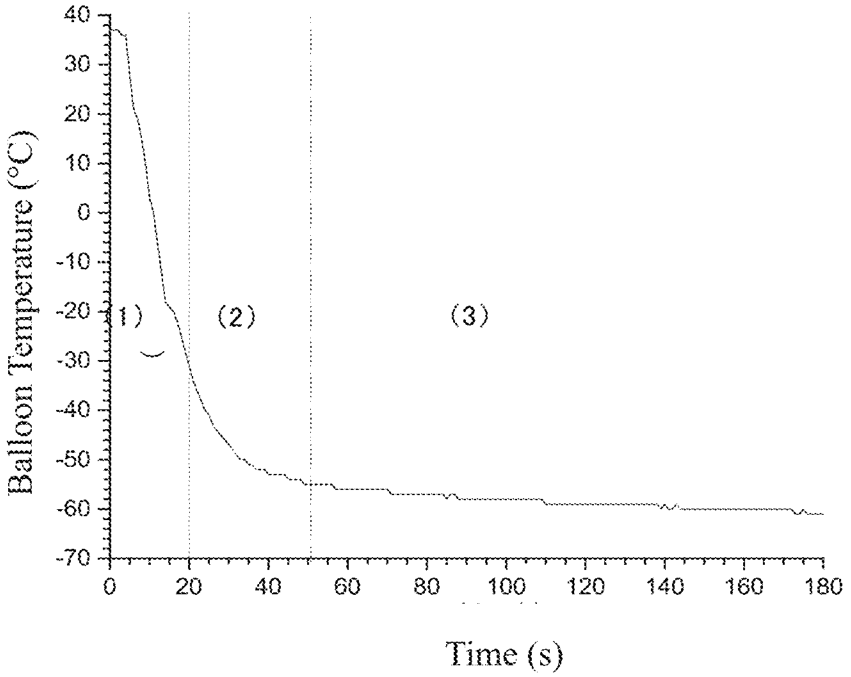
FIG. 19 schematically illustrates three phases of a cryoablation temperature profile in accordance with the present application.

In view of the above description of PID control, as shown in FIG. 19, a cryoablation control process according to embodiments of this application may be divided into three phases each adopting a different control strategy. The first phase (1) may be a rapid temperature drop phase featuring a rapid rise in flow rate with the pressure in the interior of the balloon being maintained constant until the flow rate drops to a given value. The second phase (2) may be a slow temperature drop phase in which the flow rate is maintained at the given value. The temperature of the interior of the balloon may shift to the preset target temperature phase in the third phase (3). Depending on practical clinical applications, the ablation process may employ temperature control and/or constant flow rate control, and any of these control modes may be switched to the other. The temperature control mode involves setting a target temperature value. The three phases in the control process will be described in greater detail below with reference to FIG. 19.

In the rapid temperature drop phase (1), the flow rate rises with the pressure in the interior of the balloon being maintained constant. This phase proceeds mainly with proportional-derivative (PD) with a control quantity being adjusted depending on the chosen control mode, i.e., temperature control or constant flow rate control. For example, in the former case, a target temperature may be set, and a lower target temperature may require a larger change in the opening of the high-pressure proportional valve 14, which may correspond to a pressure change in the range of 0-600 psi. The controller may employ a PD control algorithm to perform temperature control so that the flow rate ramps as quickly as possible while avoiding temperature overshoot through adjusting and controlling the proportional term according to the set target temperature. In case of flow rate control being chosen, a flow rate PD control module may divide a flow rate profile into multiple segments, and predict a slope of profile of flow rate for each of these segments. Based on the predictions, a high-pressure proportional valve PD control module may control the liquid supply flow rate of the high-pressure proportional valve 14 to gradually increase within the range of 0-7.5 l/min. In this phase, the liquid supply flow rate is controlled within an upper flow rate limit that may range from 0.5 l/min to 2 l/min, in order to avoid flow rate oscillations or overshoot. Further, in this phase, the controller may maintain the pressure in the interior of the balloon through controlling a liquid discharge flow rate of the low-pressure proportional valve 18. This control scheme enables higher flow rate control accuracy and provides a more stable liquid supply flow rate for the next phase.

In the slow temperature drop phase (2), the liquid supply flow rate of the high-pressure proportional valve 14 is maintained, with two options remaining for control of the low-pressure proportional valve 18. In the first option, the low-pressure proportional valve 18 is continually controlled so that the pressure in the interior of the balloon is maintained constant at a level over the ambient atmospheric pressure and below an upper limit for the pressure in the interior of the balloon. Moreover, in this option, a target pressure is set for the low-pressure proportional valve 18 and fed, together with values captured by the first pressure sensor 17, to the controller, which responsively calculates, according to Eqn. 1-6, respective pressure compensations for the first pressure sensor 17 so as to cause the pressure at the sensor to approach the target value. In the second option, the opening of the low-pressure proportional valve 18 is linearly incremented to a maximum value, concurrently with the pressure in the interior of the balloon rising beyond the atmospheric pressure. Then, a switch is performed to the solenoid valve 19, with the controller still controlling the liquid supply flow rate of the high-pressure proportional valve 14. This can effectively overcome the problem of significant flow rate fluctuations. In this phase, if the opening of the low-pressure proportional valve 18 is increased too rapidly, flow rate overshoot may occur. On the other hand, if the opening of the low-pressure proportional valve 18 is increased too slowly, it may take too much time for the flow rate to reach the target value. Therefore, raising the flow rate at speeds determined based on its predicted slopes can avoid flow rate fluctuations while reducing the time required for completing the procedure. For the above two control options, the controller may operate at a frequency in the range of 2-20 Hz. In this phase, when the flow rate drops too low, the controller may instruct to increase the opening of the high-pressure proportional valve to ensure a sufficient pressure in the interior of the balloon that will not lead to shrinkage thereof and hence possible tearing of the tissue against which the balloon is pressed. In this way, a stable liquid supply flow rate can be achieved while ensuring that the pressure in the interior of the balloon is maintained within a safe range.

The balloon temperature may reach and be maintained at the target temperature in the third phase (3), and this phase may last until the end of the ablation process. The preset target temperature of the interior of the balloon and the preset target flow rate may be achieved in a gradual manner by the controller using multi-stage PID control. During a cryoablation temperature control process, temperature control and flow rate control may be switched to each other so that the controller controls actions of the high-pressure proportional valve 14, the low-pressure proportional valve 18 and the solenoid valve 19 in a dynamically collaborative way to lower the temperature of the interior of the balloon to, and maintain it at, the preset target temperature and to maintain the pressure in the interior of the balloon within the safe pressure threshold value range. In practice, seamless switching between temperature control and flow rate control may be accomplished with an interface of an interactive device such as a touch screen. In traditional cryoablation control approaches that rely only on flow rate control, when a temperature of the interior of a balloon continues decreasing to a safe temperature threshold value, the process has to be interrupted, followed by a flow rate control action for avoiding causing damage to the tissue by an excessively low temperature. This requires more ablation cycles, prolongs the time of the balloon staying within the patient's body and increases surgical risk and operational complexity. Moreover, improper control may add other adverse effects to the procedure. By contrast, the switchability between flow rate control and temperature control according to this application allows dynamically maintaining the temperature of the interior of the balloon at the preset target temperature, which effectively reduces the number of required ablation cycles, shortens the time of the balloon staying within the patient's body, and allow easier operation and hence a shorter procedure time and improved pulmonary vein isolation (PVI) effects. Experiments have shown that adding the solenoid valve 19 that is controlled in a dynamically collaborative manner with the low-pressure proportional valve 18 results in temperature control accuracy that is double that of a control scheme using only the low-pressure proportional valve 18. According to this application, the resulting temperature control error is about ±1 degree, and the liquid supply flow rate is increased with a control error of approximately ±0.1 l/min, effectively avoiding flow rate fluctuations. Upon the temperature of the interior of the balloon falling into a preset temperature threshold value range, a rewarming/protection mode may be activated. For example, as soon as the temperature of the interior of the balloon drops below −60 degrees, the opening of the high-pressure proportional valve 14 may be reduced and the opening of the low-pressure proportional valve 18 may be adjusted to enable rewarming.

Figure 20:
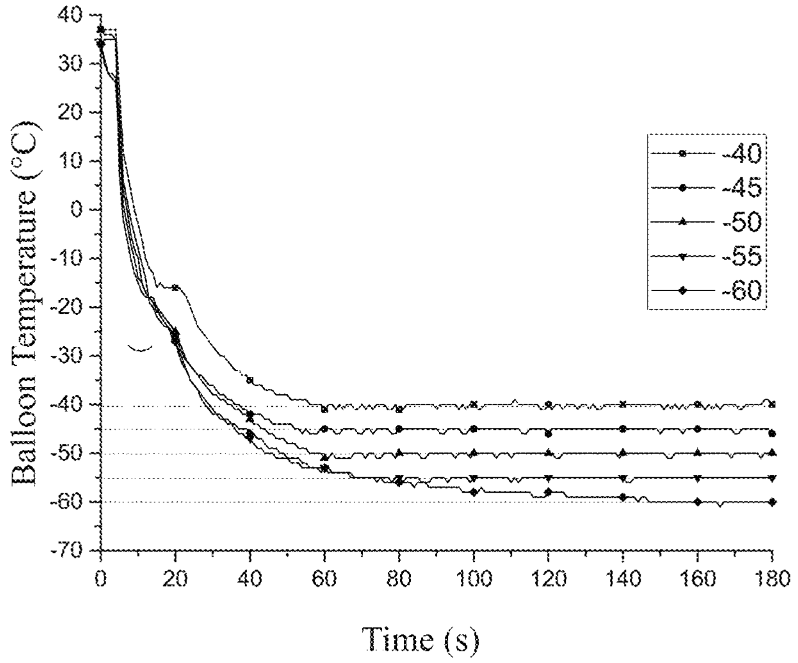
FIG. 20 schematically illustrates cryoablation temperature profiles according to embodiments of the present application.

Actual temperature profiles of the interior of a cryoablation balloon at the preset target temperatures of −40° C., −45° C., −50° C., −55° C. and −60° C. under the control of a cryoablation temperature control method using a cryoablation temperature control system according to embodiments of the present application are shown in FIG. 20. Experiments have shown that the temperature can be controlled within the range of −60° C.-−35° C. It is expressly understood that the range within which the cryoablation temperature can be controlled by the method and system of this application is not limited to that mentioned above and may vary depending on the cryogenic medium used. Various temperature ranges are possible according to the present application. However, the given temperature range can address various cryoablation applications.

In a cryoablation temperature control process according to the above embodiments, a temperature profile at the middle of the interior of a balloon may be roughly divided into three phases, and the controller may employ a multi-stage PID control algorithm to control action of the high-pressure proportional valve 14, the low-pressure proportional valve 18 and the solenoid valve 19 in a dynamically collaborative way to lower the temperature of the interior of the balloon to, and maintain it at, a preset target temperature and to maintain a pressure in the interior of the balloon within a safe pressure threshold value range. Maintaining the temperature of the interior of the balloon at the preset value leads to improved PVI effects, reduced operational complexity, a shorter procedure time and lower surgical risk.

In an embodiment of the present application, there is provide a computer-readable storage medium storing thereon a computer program, which implements, when executed by a processor, the steps in the method of any of the above-described embodiments.

The various technical features of the foregoing embodiments may be combined in any way. Although not all such combinations have been described above for the sake of brevity, any of them is considered to fall within the scope of this specification as long as there is no contradiction between the technical featured.

Presented above are merely several embodiments of the present application. Although these embodiments are described with some particularity and in some detail, it should not be construed that they limit the scope of the present application in any sense. Note that various variations and modifications can be made by those of ordinary skill in the art without departing from the concept of the present application. Accordingly, it is intended that all such variations and modifications are embraced within the scope of this application as defined in the appended claims.

What is claimed is:

1. A cryoablation temperature control method for controlling a temperature of an interior of a cryoablation balloon, the method comprising:

acquiring a real-time temperature value and a preset target temperature value of the interior of the cryoablation balloon, and generating a first temperature control signal based on the real-time and preset target temperature values;

acquiring a real-time gas flow rate value and a target gas flow rate value of a gas recovery passage in a gas outlet channel for the cryoablation balloon, and generating a first gas flow rate control signal based on the real-time and target gas flow rate values;

generating, based on the first temperature control signal and the first gas flow rate control signal, a first target liquid inlet pressure control signal for controlling a liquid supply flow rate of a high-pressure proportional valve in a liquid supply channel for the cryoablation balloon through collaboration of temperature control and flow rate control;

acquiring a real-time gas pressure value on, and a preset target gas pressure value for, a gas outlet side of the cryoablation balloon; and generating, based on the real-time and preset target gas pressure values, a first target gas outlet pressure control signal for controlling a gas outlet flow rate of a low-pressure proportional valve in the gas outlet channel for the cryoablation balloon and for controlling, together with the first target liquid inlet pressure control signal, the liquid supply flow rate of the high-pressure proportional valve; and controlling the liquid supply flow rate of the high-pressure proportional valve in the liquid supply channel and the gas outlet flow rate of the low-pressure proportional valve in the gas outlet channel for the cryoablation balloon so that the pressure in the interior of the cryoablation balloon is within the predefined safe pressure threshold value range and the temperature of the interior of the cryoablation balloon is brought to and/or maintained at the preset target temperature value to cryoablate tissue in contact with the cryoablation balloon.

2. The method of claim 1, further comprising:

generating the first temperature control signal based on the real-time and preset target temperature values using an incremental proportional-derivative (PD) or proportional-integral-derivative (PID) control algorithm;

generating the first gas flow rate control signal based on the real-time and target gas flow rate values using an incremental PD or PID control algorithm; and.

3. The method of claim 2, wherein controlling the liquid supply flow rate of the high-pressure proportional valve comprises:

acquiring a real-time liquid pressure value on a liquid outlet side of the high-pressure proportional valve; and generating a second target liquid inlet pressure control signal for controlling the liquid supply flow rate of the high-pressure proportional valve based on the first target liquid inlet pressure control signal and the real-time liquid pressure value.

4. The method of claim 2, wherein controlling the liquid supply flow rate of the high-pressure proportional valve comprises:

acquiring a real-time liquid pressure value on a liquid outlet side of the high-pressure proportional valve;

calculating a target liquid pressure value for the liquid outlet side of the high-pressure proportional valve based on the first target liquid inlet pressure control signal; and generating a second target liquid inlet pressure control signal for controlling the liquid supply flow rate of the high-pressure proportional valve based on the real-time liquid pressure value and the target liquid pressure value using an incremental PD or PID control algorithm.

5. The method of claim 1, wherein generating the first target gas outlet pressure control signal for controlling the gas outlet flow rate of the low-pressure proportional valve in the gas outlet channel for the cryoablation balloon based on the real-time and preset target gas pressure values comprises:

generating the first target gas outlet pressure control signal based on the real-time and preset target gas pressure values using an incremental PD or PID control algorithm, or linearly incrementing an opening of the low-pressure proportional valve and, upon the low-pressure proportional valve being fully open, activating a solenoid valve in the gas outlet channel for the cryoablation balloon so that at least a part of a gas discharged from the cryoablation balloon passes through the solenoid valve and then flows into the gas recovery passage.

6. The method of claim 5, further comprising:

predicting a slope of a profile of the real-time gas flow rate value to control the target gas flow rate value and dividing a temperature control process into at least two phases based on the real-time temperature value, wherein the at least two phases include a rapid temperature drop phase and a slow temperature drop phase, and wherein in the slow temperature drop phase, the real-time gas flow rate value is maintained in a predefined stable flow rate threshold value range.

7. The method of claim 1, wherein controlling the gas outlet flow rate of the low-pressure proportional valve in the gas outlet channel for the cryoablation balloon comprises:

in an event of the real-time gas flow rate value falling below a predefined flow rate threshold value range, increasing an opening of the high-pressure proportional valve so that the pressure in the interior of the cryoablation balloon is brought back into the predefined safe pressure threshold value range.

8. The method of claim 1, further comprising:

in an event of the real-time temperature value of the interior of the cryoablation balloon becoming less than or equal to a preset temperature threshold value, bringing the temperature of the interior of the cryoablation balloon back to the preset target temperature value by reducing an opening of the high-pressure proportional valve and/or adjusting an opening of the low-pressure proportional valve.

9. A cryoablation temperature control system for controlling a temperature of the interior of a cryoablation balloon, the system comprising:

a temperature sensor for capturing a real-time temperature value of the interior of the cryoablation balloon;

a high-pressure proportional valve disposed in a liquid supply channel for the cryoablation balloon;

a first pressure sensor disposed in a gas outlet channel for the cryoablation balloon, wherein the first pressure sensor is configured to capture a real-time gas pressure value on a gas outlet side of the cryoablation balloon;

a low-pressure proportional valve disposed in the gas outlet channel for the cryoablation balloon, wherein the low-pressure proportional valve is configured to adjust a pressure of a gas in the interior of the cryoablation balloon;

a flow rate sensor disposed in the gas outlet channel for the cryoablation balloon, wherein the flow rate sensor is configured to capture a real-time gas flow rate value of a gas recovery passage in the gas outlet channel for the cryoablation balloon; and a controller coupled to each of the temperature sensor, the high-pressure proportional valve, the first pressure sensor, the low-pressure proportional valve and the flow rate sensor, wherein the controller is configured to:

acquire the real-time temperature value and a preset target temperature value of the interior of the cryoablation balloon, and generate a first temperature control signal based on the real-time and preset target temperature values;

acquire the real-time gas flow rate value and a target gas flow rate value of the gas recovery passage in the gas outlet channel for the cryoablation balloon, and generate a first gas flow rate control signal based on the real-time and target gas flow rate values; and generate, based on the first temperature control signal and the first gas flow rate control signal, a first target liquid inlet pressure control signal for controlling a liquid supply flow rate of the high-pressure proportional valve in the liquid supply channel for the cryoablation balloon through collaboration of temperature control and flow rate control; and acquire a real-time gas pressure value on, and a preset target gas pressure value for, the gas outlet side of the cryoablation balloon and generate, based on the real-time and preset target gas pressure values, a first target gas outlet pressure control signal for controlling a gas outlet flow rate of the low-pressure proportional valve and for controlling, together with the first target liquid inlet pressure control signal, the liquid supply flow rate of the high-pressure proportional valve; and control the liquid supply flow rate of the high-pressure proportional valve in the liquid supply channel and the gas outlet flow rate of the low-pressure proportional valve in the gas outlet channel for the cryoablation balloon so that the pressure in the interior of the cryoablation balloon is within the predefined safe pressure threshold value range and the temperature of the interior of the cryoablation balloon is brought to and/or maintained at the preset target temperature value to cryoablate tissue in contact with the cryoablation balloon.

10. The system of claim 9, wherein the controller is further configured to:

generate the first temperature control signal based on the real-time and preset target temperature values using an incremental proportional-derivative (PD) or proportional-integral-derivative (PID) control algorithm;

generate the first gas flow rate control signal based on the real-time and target gas flow rate values using the incremental PD or PID control algorithm;

generate, based on the first temperature control signal and/or the first gas flow rate control signal, the first target liquid inlet pressure control signal for controlling the liquid supply flow rate of the high-pressure proportional valve; and acquire the real-time gas pressure value on, and the preset target gas pressure value for, the gas outlet side of the cryoablation balloon and generate, based on the real-time and preset target gas pressure values, the first target gas outlet pressure control signal for controlling the gas outlet flow rate of the low-pressure proportional valve using the incremental PD or PID control algorithm.

11. The system of claim 9, further comprising:

a second pressure sensor disposed in a liquid inlet channel for the cryoablation balloon, wherein the second pressure sensor is coupled to the controller and is configured to capture a real-time liquid pressure value on a liquid outlet side of the high-pressure proportional valve, wherein the controller is further configured to:

acquire the real-time liquid pressure value and generate, based on the first target liquid inlet pressure control signal and the real-time liquid pressure value, a second target liquid inlet pressure control signal for controlling the liquid supply flow rate of the high-pressure proportional valve.

12. The system of claim 9, wherein the controller comprises:

a parameter acquisition module configured to acquire:

the real-time temperature value and the preset target temperature value of the interior of the cryoablation balloon;

the real-time gas flow rate value and the target gas flow rate value of the gas recovery passage in the gas outlet channel for the cryoablation balloon; and the real-time gas pressure value on, and the preset target gas pressure value for, the gas outlet side of the cryoablation balloon;

a liquid supply flow rate control module configured to:

generate the first temperature control signal based on the real-time and preset target temperature values;

generate the first gas flow rate control signal based on the real-time and target gas flow rate values; and generate, based on the first temperature control signal and the first gas flow rate control signal, the first target liquid inlet pressure control signal for controlling the liquid supply flow rate of the high-pressure proportional valve in the liquid supply channel for the cryoablation balloon through collaboration of temperature control and flow rate control; and a gas outlet pressure control module configured to generate, based on the real-time and preset target gas pressure values, the first target gas outlet pressure control signal for controlling the gas outlet flow rate of the low-pressure proportional valve in the gas outlet channel for the cryoablation balloon, wherein the liquid supply flow rate control module and the gas outlet pressure control module coordinate with each other to perform control so that the pressure in the interior of the cryoablation balloon is within the predefined safe pressure threshold value range and the temperature of the interior of the cryoablation balloon is brought to and/or maintained at the preset target temperature value.

13. The system of claim 12, wherein the parameter acquisition module is further configured to:

acquire a real-time liquid pressure value on a liquid outlet side of the high-pressure proportional valve, wherein the liquid supply flow rate control module comprises:

a temperature PD/PID control module configured to generate the first temperature control signal based on the real-time and preset target temperature values using an incremental PD or PID control algorithm;

a gas flow rate PD/PID control module configured to generate the first gas flow rate control signal based on the real-time and target gas flow rate values using the incremental PD or PID control algorithm; and a high-pressure proportional valve PD/PID control module configured to:

generate the first target liquid inlet pressure control signal based on the first temperature control signal and/or the first gas flow rate control signal;

calculate a target liquid pressure value for the liquid outlet side of the high-pressure proportional valve based on the first target liquid inlet pressure control signal; and generate, based on the real-time and target liquid pressure values using an incremental PD or PID control algorithm, a second target liquid inlet pressure control signal for controlling the liquid supply flow rate of the high-pressure proportional valve, wherein the gas outlet pressure control module comprises:

a low-pressure proportional valve PD/PID control module configured to generate, based on the real-time and preset target gas pressure values using the incremental PD or PID control algorithm, the first target gas outlet pressure control signal for controlling the gas outlet flow rate of the low-pressure proportional valve, and wherein the temperature PD/PID control module, the gas flow rate PD/PID control module, the high-pressure proportional valve PD/PID control module and the low-pressure proportional valve PD/PID control module coordinate with one another to perform control so that the pressure in the interior of the cryoablation balloon is within the predefined safe pressure threshold value range and the temperature of the interior of the cryoablation balloon is brought to and/or maintained at the preset target temperature value.

14. The system of claim 9, wherein the controller is further configured to:

in an event of the real-time temperature value of the interior of the cryoablation balloon becoming less than or equal to a preset temperature threshold value, bringing the real-time temperature value of the interior of the cryoablation balloon back to the preset target temperature value through reducing an opening of the high-pressure proportional valve and/or adjusting an opening of the low-pressure proportional valve.

* * * * *